US009808594B2

United States Patent
Dantanarayana et al.

(10) Patent No.: US 9,808,594 B2
(45) Date of Patent: Nov. 7, 2017

(54) FLOW REGULATION VENT

(71) Applicant: ResMed Limited, Bella Vista, New South Wales (AU)

(72) Inventors: Muditha Pradeep Dantanarayana, Sydney (AU); Saad Nasr, Sydney (AU)

(73) Assignee: RESMED LIMITED, Bella Vista (AU)

( * ) Notice: Subject to any disclaimer, the term of this patent is extended or adjusted under 35 U.S.C. 154(b) by 0 days.

(21) Appl. No.: 15/298,474

(22) Filed: Oct. 20, 2016

(65) Prior Publication Data

US 2017/0049988 A1      Feb. 23, 2017

Related U.S. Application Data

(63) Continuation of application No. 15/001,521, filed on Jan. 20, 2016, which is a continuation of application
(Continued)

(51) Int. Cl.
*A61M 16/20* (2006.01)
*A61B 5/08* (2006.01)
(Continued)

(52) U.S. Cl.
CPC ......... *A61M 16/208* (2013.01); *A61B 5/0876* (2013.01); *A61M 16/0057* (2013.01);
(Continued)

(58) Field of Classification Search
CPC . A61B 5/0876; A61M 15/00; A61M 15/0016; A61M 15/002; A61M 15/0028;
(Continued)

(56) References Cited

U.S. PATENT DOCUMENTS 3,050,998 A    8/1962  Dahlke
3,574,362 A    4/1971  Gregg et al.
(Continued)

FOREIGN PATENT DOCUMENTS

DE    41 42 295 A1    7/1993
DE    198 01 545 A1   8/1999
(Continued)

OTHER PUBLICATIONS

Extended European Search Report dated Feb. 17, 2011 in European Application No. 10185006.3 (6 pages).
(Continued)

*Primary Examiner* — Annette Dixon
(74) *Attorney, Agent, or Firm* — Nixon & Vanderhye, P.C.

(57) ABSTRACT

A flow regulation vent for use in controlling a vent flow of washout gas in a system for supplying breathable gas pressurized to within a therapeutic pressure range above atmospheric pressure to a patient in the treatment of a sleep disordered breathing condition is disclosed. The flow regulation vent may include a housing having at least one vent orifice and at least one fixed bleed orifice; and a flap configured to regulate the vent flow of washout gas through the at least one vent orifice, wherein the at least one fixed bleed orifice is not covered by the flap in any position and the flow regulation vent provides a minimum vent flow independent of the position of the flap.

30 Claims, 22 Drawing Sheets

Related U.S. Application Data

No. 13/891,237, filed on May 10, 2013, now Pat. No. 9,278,186, which is a continuation of application No. 10/433,980, filed as application No. PCT/AU01/01658 on Dec. 21, 2001, now Pat. No. 8,439,035.

(60) Provisional application No. 60/257,171, filed on Dec. 22, 2000.

(51) Int. Cl.
| | | |
|---|---|---|
| *A61M 16/06* | (2006.01) | |
| *A61B 5/087* | (2006.01) | |
| *G01F 1/28* | (2006.01) | |
| *A61M 16/08* | (2006.01) | |
| *A61M 16/00* | (2006.01) | |

(52) U.S. Cl.
CPC ........ *A61M 16/06* (2013.01); *A61M 16/0616* (2014.02); *A61M 16/0622* (2014.02); *A61M 16/0633* (2014.02); *A61M 16/0816* (2013.01); *A61M 16/0825* (2014.02); *A61M 16/0875* (2013.01); *G01F 1/28* (2013.01); *A61M 2016/0042* (2013.01); *A61M 2205/332* (2013.01); *A61M 2205/42* (2013.01); *A61M 2210/0618* (2013.01)

(58) Field of Classification Search
CPC .............. A61M 16/00; A61M 16/0048; A61M 16/0057; A61M 16/0069; A61M 16/06; A61M 16/0633; A61M 16/0666; A61M 16/08; A61M 16/1065; A61M 16/20; A61M 16/202; A61M 16/208; A61M 16/209; A61M 39/00; A61M 39/22–39/26; A62B 7/00; A62B 7/12; A62B 9/00; A62B 9/02; B60H 1/24; B60H 1/249; B60R 19/24; B60R 19/32; E03F 3/04; E03F 5/00; E03F 5/22; F02N 17/00; F02N 17/06; F02N 19/10; F04B 39/10; F04B 39/1073; F16K 11/02; F16K 11/052; F16K 15/02; F16K 15/03; F16K 15/14; F16K 15/144; F16K 15/16; F16K 31/44; F16K 31/56; F16K 31/563; F16L 41/02; G01F 1/28; G05D 7/00; G05D 7/01; G05D 7/012; G05D 7/0126
USPC ............ 128/200.14, 200.24, 201.11, 201.22, 128/201.23, 201.25, 201.28, 202.27, 128/202.28, 202.29, 203.11, 203.12, 128/203.14, 203.15, 203.23, 203.24, 128/204.18, 204.19, 204.21, 204.22, 128/204.23, 204.24, 204.25, 204.26, 128/205.11, 205.12, 205.23, 205.24, 128/205.25, 205.27, 205.28, 205.29, 128/206.12, 206.15, 206.16, 206.17, 128/206.18, 206.19, 206.21, 206.23, 128/206.24, 206.26, 206.27, 206.28, 128/207.12, 207.13, 207.14, 207.16, 128/207.17, 207.18, 206.22
See application file for complete search history.

(56) References Cited

U.S. PATENT DOCUMENTS

| | | | |
|---|---|---|---|
| 3,796,216 A | 3/1974 | Schwarz | |
| 3,920,274 A | 11/1975 | Fannin | |
| 4,009,366 A | 2/1977 | Danell | |
| 4,230,149 A | 10/1980 | Worthen et al. | |
| 4,284,075 A | 8/1981 | Krasberg | |
| 4,854,574 A | 8/1989 | Larson et al. | |
| 5,285,816 A | 2/1994 | Herlihy | |
| 5,295,478 A | 3/1994 | Baldwin | |
| 5,438,981 A | 8/1995 | Starr et al. | |
| 5,465,712 A | 11/1995 | Malis et al. | |
| 5,647,355 A | 7/1997 | Starr et al. | |
| 5,655,898 A | 8/1997 | Hashimoto et al. | |
| 5,657,752 A | 8/1997 | Landis et al. | |
| 5,685,296 A | 11/1997 | Zdrojkowski et al. | |
| 5,727,546 A | 3/1998 | Clarke et al. | |
| 5,743,289 A | 4/1998 | Griffin et al. | |
| 5,896,857 A | 4/1999 | Hely et al. | |
| 5,970,801 A | 10/1999 | Ciobanu et al. | |
| 6,006,748 A | 12/1999 | Hollis | |
| 6,035,896 A | 3/2000 | Liardet et al. | |
| 6,189,532 B1 | 2/2001 | Hely et al. | |
| 6,210,514 B1 | 4/2001 | Cheung et al. | |
| 6,253,764 B1* | 7/2001 | Calluaud ............... A61M 16/20 128/204.18 |
| 6,581,594 B1 | 6/2003 | Drew et al. | |
| 6,983,556 B2 | 1/2006 | McMullin | |
| 8,113,197 B2* | 2/2012 | Smart .................. A61M 16/06 128/202.26 |
| 8,136,524 B2 | 3/2012 | Ging et al. | |
| 8,439,035 B2* | 5/2013 | Dantanarayana .... A61B 5/0876 128/203.11 |
| 9,278,186 B2* | 3/2016 | Dantanarayana .... A61B 5/0876 |
| 2002/0153012 A1 | 10/2002 | Gunaratnam et al. | |
| 2002/0174867 A1 | 11/2002 | Gunaratnam et al. | |
| 2003/0005931 A1 | 1/2003 | Jaffre | |
| 2003/0196656 A1 | 10/2003 | Moore et al. | |
| 2003/0196657 A1 | 10/2003 | Ging | |
| 2004/0094157 A1 | 5/2004 | Dantanarayana et al. | |
| 2004/0112385 A1 | 6/2004 | Drew | |
| 2004/0255948 A1 | 12/2004 | Smith et al. | |
| 2010/0236549 A1 | 9/2010 | Selvarajan et al. | |
| 2013/0008439 A1 | 1/2013 | Selvarajan et al. | |
| 2013/0239971 A1 | 9/2013 | Dantanarayana | |
| 2016/0129214 A1 | 5/2016 | Dantanarayana et al. | |

FOREIGN PATENT DOCUMENTS

| | | |
|---|---|---|
| EP | 0 710 488 A | 5/1996 |
| EP | 1525895 | 4/2005 |
| FR | 1 457 820 A | 1/1967 |
| GB | 1 555 016 | 11/1979 |
| GB | 2 121 185 A | 12/1983 |
| JP | 1-70119 | 5/1989 |
| JP | 2-223822 | 9/1990 |
| JP | 9-501581 | 2/1997 |
| WO | WO 93/24181 | 12/1993 |
| WO | WO 97/05824 | 2/1997 |
| WO | 98/26830 | 6/1998 |
| WO | WO 98/23318 | 6/1998 |
| WO | 00/38772 | 7/2000 |
| WO | WO 00/38772 | 7/2000 |
| WO | 02/051486 | 7/2002 |
| WO | 02/096342 | 12/2002 |
| WO | 2005/063326 | 7/2005 |
| WO | 2005/063328 A1 | 7/2005 |
| WO | 2006/122369 | 11/2006 |
| WO | 2006/130903 A1 | 12/2006 |
| WO | 2007/045008 A1 | 4/2007 |

OTHER PUBLICATIONS

Examination Report dated Jul. 22, 2015 issued in European Application No. 10 185 006.3 (8 pages).
Communication dated Mar. 7, 2013 in European Application No. 06 704 169.9 (4 pages).
International Search Report for PCT/AU2006/000031 dated Mar. 23, 2006.
Office Action dated Mar. 28, 2011 in European Application No. 06 704 169.9 (5 pages).
Third Party Observations dated Mar. 25, 2011 in European Application No. 06 704 169.9, (2 pages).
European Search Report issued in EP Application No. 06704169.9, dated Mar. 4, 2010, (7 pages).

(56) References Cited

OTHER PUBLICATIONS

Supplementary European Search Report from EP 01 27 1909, dated Feb. 8, 2006, (3 pages).
Japanese Office Action ("Notice of Reasons for Rejection") issued in JP Application No. 2002-552627 with English translation, dated Dec. 4, 2007, (4 pages).

* cited by examiner

FLOW REGULATION VENT

This application is a continuation of U.S. patent application Ser. No. 15/001,521, filed Jan. 20, 2016, pending, which is a continuation of U.S. patent application Ser. No. 13/891,237, filed May 10, 2013, now U.S. Pat. No. 9,278,186, which is a continuation of U.S. patent application Ser. No. 10/433,980, filed Jun. 10, 2003, now U.S. Pat. No. 8,439,035, which is the U.S. national phase of International Application No. PCT/AU01/01658, filed Dec. 21, 2001, and claims priority to U.S. Provisional Application No. 60/257,171, filed Dec. 22, 2000, the entire contents of each of which are hereby incorporated by reference.

FIELD OF THE INVENTION

The present invention relates to a vent valve apparatus for use with a system for supplying breathable gas pressurized above atmospheric pressure to a human.

The invention has been developed primarily for use in controlling the venting of washout gas in a continuous positive airway pressure (CPAP) gas delivery systems used, for example, in the treatment of obstructive sleep apnea (OSA) and similar sleep disordered breathing conditions. The invention may also be used in conjunction with suitable mask and gas delivery systems for the application of assisted ventilation treatment.

The term "mask" is herein intended to include face masks, nose masks, mouth masks, appendages in the vicinity of any of these masks and the like.

BACKGROUND OF THE INVENTION

Treatment of OSA by CPAP gas delivery systems involves the continuous delivery of air (or breathable gas) pressurized above atmospheric pressure to a patient's airways via a conduit and a mask. CPAP pressures of 4 cm $H_2O$ to 30 cm $H_2O$ are typically used for treatment of sleep disordered breathing due to OSA and/or central apnea, depending on patient requirements.

Treatment pressures for assisted ventilation can range up to 32 cm $H_2O$ and beyond, depending on patient requirements.

For either the treatment of OSA or the application of assisted ventilation, the pressure of the gas delivered to patients can be constant level, bi-level (in synchronism with patient inspiration and expiration) or automatically adjusting in level. Throughout this specification the reference to CPAP is intended to incorporate a reference to any one of, or combinations of, these forms of pressure delivery. The prior art method for providing CPAP treatment includes a vent for gas washout of the gas flow. The vent is normally located at or near the mask or in the gas delivery conduit. The flow of gas through the vent is essential for removal of exhaled gases from the breathing circuit. Adequate gas washout is achieved by selecting a vent size and configuration that will allow a minimum safe gas flow at the lowest operating CPAP pressure, which typically can be as low as, around 4 cm $H_2O$ for adults and 2 cm $H_2O$ in pediatric applications.

Existing vent configurations include single or multiple holes, foam or other diffusers, slots and combinations thereof. A reference herein to a vent may be understood to include a reference to one or more holes, foam or other diffusers, slots or any combination of them.

It is obviously desirable for a CPAP system to have as wide a pressure range as is feasible in order that a standard configuration may adequately provide the unique treatment require by a variety of users. Increasing CPAP pressure results in more gas passing through the vent which in turn creates more noise. Existing prior art vents can produce excessive noise when CPAP pressures are raised above about 4 cm $H_2O$. This noise can adversely affect patient and bed-partner comfort. At higher pressures, existing vents are also inefficient as they allow more gas through the vent than is required for adequate exhaust gas washout and thereby require the flow generator to provide more flow than is necessary in order to maintain the required treatment pressure. Further, where treatment gas is being supplied, such as oxygen, surplus treatment gas is vented and thereby wasted unnecessarily. A similar waste occurs where the supplied gas is humidified.

The flow of gas from the gas delivery system through the vent to atmosphere creates noise as the delivered gas, and upon expiration the patient expired gas including $CO_2$, passes through the vent to atmosphere. A CPAP system must have a rate of flow through the vent to atmosphere that ensures a clinically undesirable level of expired gas is not retained within the breathing circuit (i.e. within the gas supply conduit and mask chamber). This retention occurs as a result of the exhaled gas not being vented to atmosphere during the exhalation phase of respiration but rather moving down the gas conduit towards the flow generator or accumulating within the mask chamber dead space. An adequate flow of gas to atmosphere may be achieved by selecting the suitable vent size for the clinically desirable pressure treatment range and volume of gas made available by the flow generator to achieve the desired treatment pressure range. Typically this selection involves a compromise being struck between the choice of a vent size that is sufficiently large to achieve an adequate flow rate at the low end of the pressure range and yet cause no greater than an acceptable noise level as the pressure increases through the pressure range. In addition, a large vent which would allow for a generous wash out flow rate at the low end of the pressure range will dictate that the flow generator must have adequate capacity to provide the flow necessary to achieve the desired pressures higher in the pressure range. In short, where the vent size is chosen to deliver a quiet gas wash out flow rate at the higher pressure levels of the pressure range it may be inadequate to allow acceptable wash out flow at the desired lowest end of the pressure range. Also a vent with sufficient size to achieve an adequate wash out flow rate at pressures low in the pressure range tend to generate unacceptable noise at the desired higher end of the pressure range. In addition the choice of a larger vent dictates that the source of gas have capacity to deliver the requisite flow rates for the higher pressure levels and as such the gas source will tend to consume more power and generate louder noise and require additional noise attenuating features so as to keep the total noise within acceptable limits.

Because of the constraints on CPAP system design arising from the vent a choice may be made to limit the lower or upper achievable pressure i.e. for a given upper or lower pressure the delta P between that pressure and the other extreme of the range may be inconveniently constrained. The delta P would be chosen so as to achieve the desired aims of adequate wash out of exhaled gas at the lowest end of the pressure range while capping the noise generated and power consumed at the higher end of the pressure range. Such limitations on the choice of upper or lower pressures and the delta P can seriously confine the usefulness of CPAP system as it is desirable for a standard configuration to have the capacity to deliver the widest pressure range so as to be capable of meeting the clinical requirement of as many users as possible. Achievement of this aim is particularly significant where the CPAP treatment involves the operation of a control algorithm that varies the pressure delivered to the user during the period of treatment (for example on a breath-by-breath basis between two or more pressures or in a more complex manner during the period of treatment). Similarly a computer controlled CPAP system that varies the pressure during the period of treatment in accordance with a control algorithm will include operating parameters which reflect the vent characteristic of the breathing circuit. Because of this it can be undesirable to change from a mask specified for the control algorithm for concern that the new mask should introduce a vent characteristic which is not within the operating parameters of the control algorithm. This inability to change masks because of the accompanying introduction of unknown or incompatible vent characteristics can be adverse to patient compliance with CPAP treatment. This is because a patient may only tolerate CPAP treatment where it is delivered through a particular mask and that mask is incompatible with the prescribed CPAP system control algorithm. Accordingly another aim of the present invention is to provide for a method of configuring and making a vent which can change the vent characteristic of a mask so that the mask may better comply with the operating parameters of a CPAP system control algorithm.

A further aim of the present invention is a method and apparatus for a system of venting which creates a vent having a flow area which varies with changes in pressure occurring at part of or the whole of a CPAP system pressure operating range.

It is known in the art for a CPAP system breathing circuits to include valves that restrict or block venting to atmosphere in given circumstances.

U.S. Pat. No. 5,685,296 to Zdrojkowski discloses a Flow Regulating Valve and Method. In the first embodiment, a rigid insert 52 having a central axial opening 54 is connected to a resilient diaphragm 42. As gas supply pressure increases, the diaphragm 42 flexes toward valve body member 38 and opening 54 moves over a body portion 70 of regulating pin 62, thereby decreasing the flow area between opening 54 and regulating pin 62 and maintaining a relatively constant gas flow rate even at the higher gas pressure. In additional embodiments, gas supply pressure is used to move flexible diaphragms 42' and 42" toward respective valve body walls, thereby decreasing the gas flow areas between the respective diaphragms and the valve body walls and preventing higher gas flows at higher gas pressures.

U.S. Pat. No. 6,006,748 to Hollis discloses a Vent Valve Apparatus which is adapted to progressively restrict a flow area of a washout vent as the pressure of the gas supply increases. In two embodiments disclosed therein, a flexible diaphragm 20 sensitive to the pressure of the gas supply is connected by a rigid wire rod 23 to a conical plug 18 positioned in a conical orifice 15. As the pressure of the gas supply increases, the diaphragm 20 bulges outward. This moves the rod 23 and conical plug 18 such that the conical plug 18 is drawn into the orifice 15, thereby decreasing the flow area of the vent between the plug 18 and orifice 15 and restricting the flow of gasses through the vent. In a third embodiment, an aerodynamic wing 30 replaces the diaphragm 20 and moves the conical plug in relation to gas flow past the aerodynamic surfaces of the wing.

While each of these references discloses embodiments that restrict gas flow as the pressure of the gas supply increases, there is a desire to provide a flow regulation vent that is simpler and cheaper to manufacture while providing the opportunity to have the flow through the vent vary as the pressure varies in a manner that is not limited to achieving a constant flow rate.

These valves are generally known as non-rebreath or anti-asphyxia valves. An example of a non-rebreath valve is U.S. Pat. No. 5,438,981 to Starr et al. for an Automatic Safety Valve And Diffuser For Nasal And/Or Oral Gas Delivery Mask which includes a valve element 32 that can pivot between a first position and a second position to allow inflow into a mask from either a gas flow generator or the atmosphere. The safety valve does not restrict gas flow as the pressure of the gas supply increases.

Other examples of safety valves can be found in U.S. Pat. Nos. 5,896,857, 6,189,532 (Hely/Lithgow assigned to ResMed Limited) and WO 00/38772 (Walker et. al assigned to ResMed Limited).

An embodiment of the vent of the present invention could also serve as a non-rebreath or antiasphyxia valve.

SUMMARY OF THE INVENTION

The present invention is a flow regulation vent for regulating flow from a pressurized gas supply. The vent includes a fixed portion adapted to engage a gas supply conduit and a spring force biased movable portion connected by a hinge to the fixed portion and flowingly connected to the pressurized gas supply. The fixed portion includes a gas flow orifice. The movable portion is pivotally movable between a relaxed position and a fully pressurized position. At a specified minimum operating pressure, the movable portion is pivoted by the spring force away from the fixed portion to the relaxed position to establish a first gas flow area between the movable portion and the gas flow orifice. At a specified greater operating pressure, the pressurized gas offsets the spring force to pivot the movable portion to the fully pressurized position adjacent the fixed portion to establish a minimum gas flow area between the movable portion and the gas flow orifice. In a preferred embodiment, the fixed portion and the movable portion are unitarily formed from a single piece of material, such as a sheet of stainless steel or a sheet of plastic.

By tuning the operating characteristics of the flow regulation vent (i.e. the size of the gas flow orifice at a given pressure), the flow rate curve (being the flow through the vent) can be tailored to be relatively constant across a specified operating pressure range or to be a non-constant flow curve over a specified operating pressure range.

In a further embodiment, the flow regulation vent can operate as a flow meter by including a strain gauge mounted between the fixed portion and the movable portion for measuring the position of the movable portion and providing an indicator of flow through the vent. The signal generated by the strain gauge transducer will be used with the pressure to determine the flow of gas through the vent.

In an alternative embodiment of the present invention the flow regulation vent includes a flexible flap portion having a portion engaging or attached to a fixed housing so that a free portion of the flap can move within a given range with respect to the housing. One side of the flap is exposed to an interior of the mask shell or gas flow conduit that is pressurized when the CPAP system mask is in use and another side is positioned toward an atmosphere side of the vent.

The housing includes a vent orifice positioned beneath the free portion of the flap with a portion of the housing surrounding the vent orifice being curved. While flexible, the flap has a level of natural rigidity that will provide a spring resistance against bending of the flap. In a relaxed state, the free portion of the flap will leave the vent orifice uncovered and a gas flow area between the vent orifice and the flap will be at a maximum. When the CPAP system is in use a force will act against the spring resistance of the flap and the free portion of the flap will tend to move toward the vent orifice. As the free portion of the flap moves closer to the vent orifice with increasing mask pressure, it follows the curved surface of the housing, progressively closing the vent orifice and reducing the gas flow area between the vent orifice and the flap. The interaction between the increasing mask pressure and decreasing gas flow area acts to reduce the gas flow rate through the vent as compared to the flow that would be achieved with a vent of constant gas flow area.

An alternative embodiment of the flow regulation vent of the present invention opens an auxiliary exhalation vent orifice during exhalation to allow higher exhalation gas flow to atmosphere. An embodiment may also include a non-rebreath valve or anti-asphyxias valve function that reduces or eliminates exhaled gas being retained in the gas circuit after the end of exhalation. These embodiments serve the desired aim of eliminating or at least reducing the occurrence of a user rebreathing exhaled gas.

In yet another embodiment the vent of the present invention could be configured so as to facilitate the retention in the mask of a desired level of exhaled breath including $CO_2$. The desired level of retention would be directed towards augmenting a prescribed treatment, where some $CO_2$ retention may serve to counter the patient's own excessive exhalation of $CO_2$.

The flow regulation vent of the present invention is simple and inexpensive to manufacture but provides effective, easily tailored flow regulation. The flow regulation vent reduces operating noise of the CPAP system by reducing the volume of gas flow required from the flow generator at high pressures, as well as thus reducing the work output of the flow generator. The vent also reduces rebreathing of $CO_2$ and other exhaled gas and provides for faster air pressure rise time, increasing the effectiveness of the CPAP system and patient compliance with CPAP treatment.

The invention will now be described in detail in conjunction with the following drawings in which like reference numerals designate like elements.

DETAILED DESCRIPTION OF THE PREFERRED EMBODIMENTS

Figure 1:
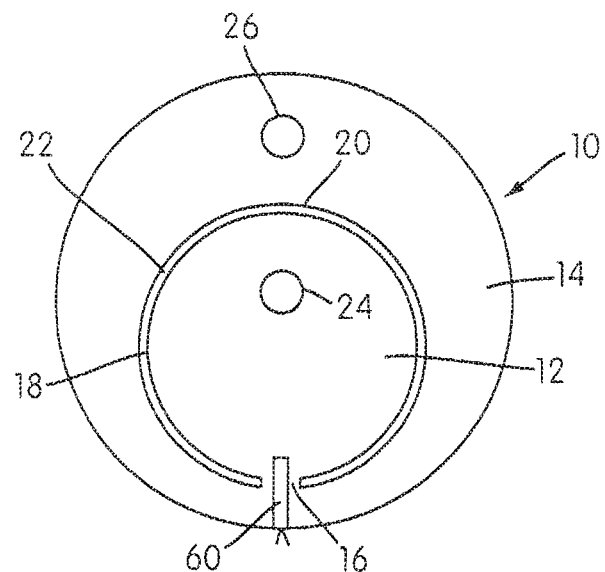
FIG. 1 is a top plan view of the flow regulation valve of the present invention.
Figure 2:
FIG. 2 is a side plan view of the flow regulation valve of FIG. 1 in a fully pressurized position.
Figure 3:
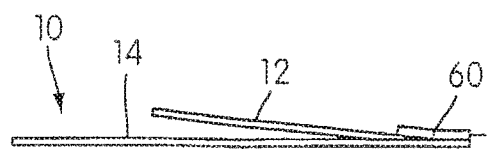
FIG. 3 is a side plan view of the flow regulation valve of FIG. 1 in a relaxed position.

A flow regulation vent 10 is shown in FIGS. 1-3, and, in this embodiment, is circular. The flow regulation vent 10 is constructed from a unitary sheet of material and includes a movable portion 12 pivotally attached at one end to a fixed portion 14 by unitary hinge 16. Movable portion 12 has an outer perimeter 18, which, in the embodiment shown, is substantially circular. Fixed portion 14 includes an orifice 20, which, in the embodiment shown, is also substantially circular and which is slightly larger in diameter than the diameter of the outer perimeter 18 to provide a gap 22 therebetween when the movable portion is in a fully pressurized position. See FIG. 2, which shows a side view of the vent 10 when in the fully pressurized position. Movable portion 12 can optionally include one or more bleed orifices 24 and fixed portion 14 can optionally include one or more bleed orifices 26.

Figure 4:
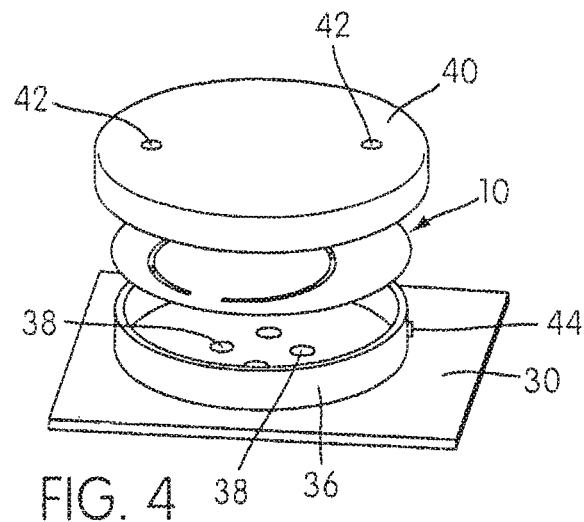
FIG. 4 is an exploded perspective view of the flow regulation valve of the FIG. 1 in combination with base and cover.
Figure 5:
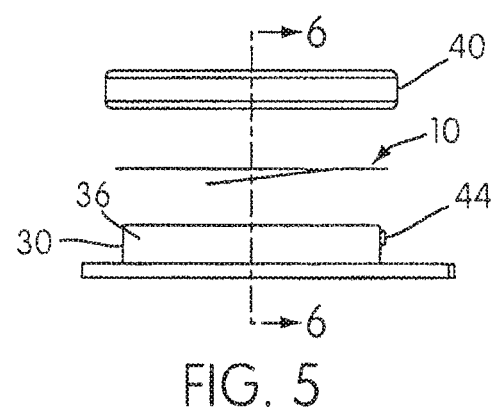
FIG. 5 is a side plan view of the exploded view of FIG. 4.
Figure 6:
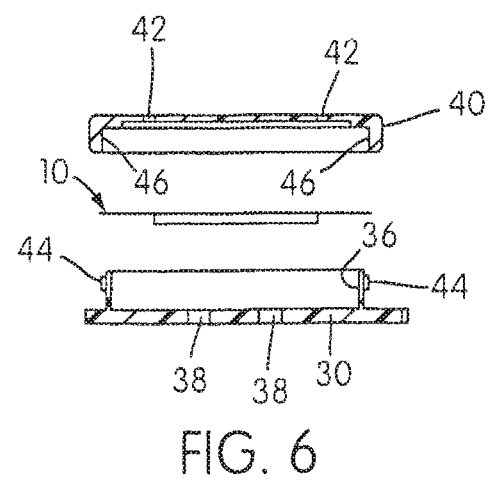
FIG. 6 is a sectional view taken along section line 6-6 in FIG. 5.

FIG. 4 shows the flow regulation vent 10 in an exploded perspective view in combination with a base portion 30 and a cover 40. The base portion 30 can be an integral part of a breathing mask shell 32 for covering the mouth and/or nostrils of the patient 50 (see FIG. 7) or can be an integral part of a gas flow tube or conduit 34 that connects the shell 32 to a pressurized gas supply (see FIG. 8). Alternatively, the base portion 30 can be a separate unit attachable to the shell 32 or tube 34. The base portion 30 includes a support ring 36 that supports an outer periphery of the vent 10 and one or more orifices 38 for connecting the vent 10 to the pressurized gas supply. Alternatively, the bottom of the base portion can be open to the mask shell or gas conduit, but the utilization of a floor with orifices 38 is preferred when the vent 10 is mounted to the mask shell to reduce access to the vent 10 from the interior of the mask shell and prevent accidental damage to the vent 10 from the interior of the mask shell. The cover 40 fits over and is connected to the base portion 30 to fix the vent in place. The cover includes one or more orifices 42 for venting gas to the atmosphere from the vent 10. The number, size, positioning and shape of the orifices 38 and 42 can be altered as appropriate for the specific application to alter gas flow and noise levels. In the preferred embodiment, cover 40 has 18 orifices of 1.2 mm diameter to provide a level of noise reduction. Alternatively, the cover 40 can be made of a wire mesh or other mesh such as in accordance with co-pending U.S. patent application Ser. No. 09/570,907 filed May 15, 2000 presently unpublished the contents of which are incorporated herein by reference. The cover can be attached to the base portion in any known manner, including snap-fit, screw-on or glued. The snap-fit or screw-on connection is preferred since this provides for ease of cleaning or replacing the vent 10. FIGS. 4 and 5 show projections 44 on support ring 36 that can engage an indentation 46 on the interior of the cover 40 to provide a snap-fit.

Figure 7:
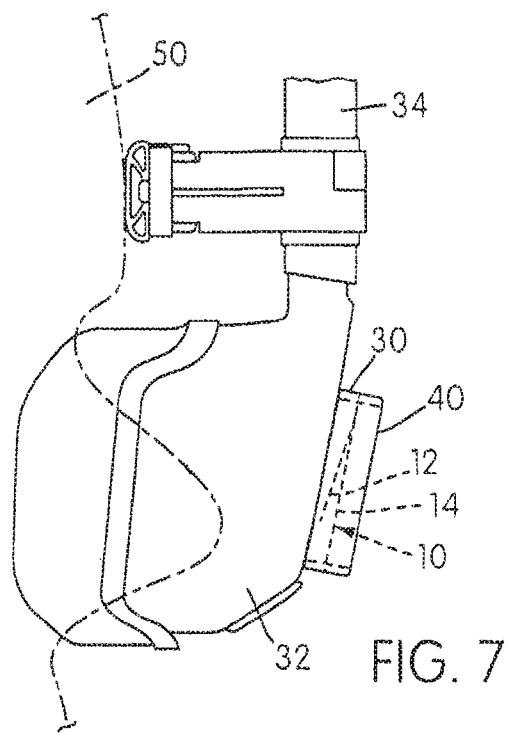
FIG. 7 is a side plan view of the flow regulation vent of FIG. 1 attached to a shell of a breathing mask.
Figure 8:
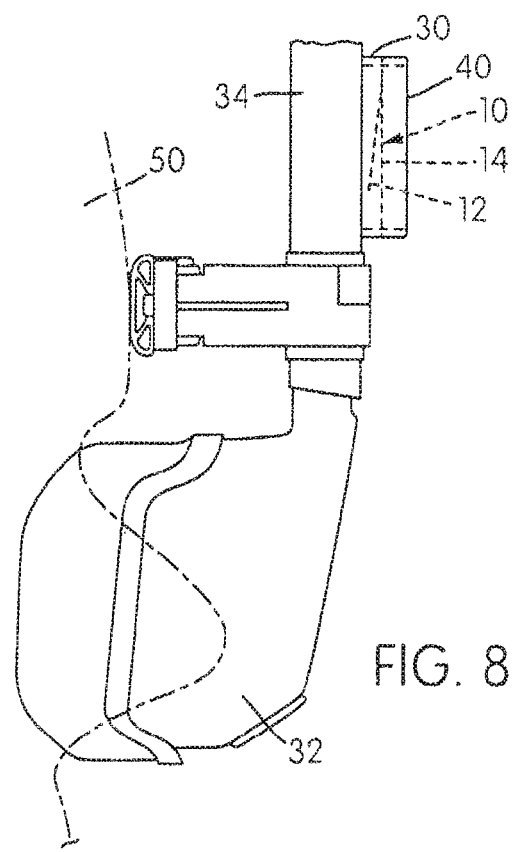
FIG. 8 is a side plan view of the flow regulation vent of FIG. 1 attached to a gas supply tube connecting a shell of a breathing mask to a pressurized gas supply.

As can be seen in FIGS. 5, 7 and 8, in the relaxed position, the movable portion 12 of vent 10 (shown in phantom) is pivoted away from the fixed portion 14 toward the mask shell 32 or gas supply tube 34, i.e. towards the pressurized gas supply and away from the atmosphere.

The operation of the flow regulation vent 10 will now be described. At the minimum safe gas flow at the lowest operating CPAP pressure of, say, 2-4 cm $H_2O$, the movable portion 12 is biased by the force from the spring hinge 16 into a relaxed position pivoted away from the fixed portion 14 and toward the pressurized gas supply. See FIGS. 3, 7 and 8. This provides a maximum gas flow area between the movable portion 12 and the orifice 20. Thus, at such a low pressure, the flow area is maximized for allowing gas to easily vent from the mask shell 32 to the atmosphere. This design can also act as an anti-asphyxia valve designed to be open with a large flow area to the atmosphere at low or no pressure. For instance, if the flow generator stops working due to a malfunction, the vent 10 remains open, allowing the patient to continue breathing while reducing the risk of asphyxiation, or even the perception thereof, by the patient. A specific flow area is required for the achievement of an anti-asphyxia effect that is usually larger than would be necessary to achieve the lower end of the pressure range during normal operation. Therefore, an antiasphyxia embodiment can be designed to include an even larger flow area that is fully exposed and provides an adequate anti-asphyxia effect when there is no pressure in the system (as is the case when there is a failure of power or the flow generator and when the anti-asphyxia effect is required). That specific flow area would then close somewhat when the CPAP system is operating as intended at the lowest/lower pressure range and from there the movable portion continues to reduce the flow area as designed with increasing pressure.

However, as CPAP pressure increases, a force acts on the surface of the movable portion 12 to counteract the force of the spring hinge 16 and move the movable portion 12 toward the fixed portion 14. This action causes a continuous reduction in the gas flow area between the movable portion 12 and the orifice 20. Once the maximum designed operating pressure is reached, the gas flow area between the movable portion 12 and the orifice 20 is at a minimum. A further increase in pressure will not lead to a further reduction of the gas flow area. In the preferred embodiment, the minimum gas flow area is achieved when the movable portion 12 and the fixed portion 14 are essentially coplanar, i.e. lie in the same plane, and the gap 22 between the orifice 20 and the outer periphery 18 of movable portion 12 is minimized. See FIG. 2.

Thus, by the present invention, a gas flow area for allowing gas to escape from the CPAP system to atmosphere is reduced as the pressure of the gas supply increases. In this way, the total flow rate for gas from the CPAP system is reduced (as compared to a fixed gas flow area vent) even though the pressure of the gas is increasing. Through appropriate tuning of the flow regulation vent 10 within a specified operating pressure range of the CPAP system, a desired flow rate curve can be obtained, including a flow rate curve that is substantially flat across the specified operating pressure range. In alternative embodiments, the flow regulation vent 10 can be tuned to provide an increasing flow rate curve or even a decreasing flow rate curve, if the specific application warrants such, or even different combinations of flat, rising and falling curves at different segments within the specified operating range.

The flow regulation vent 10 can be tuned to deliver differing flow rate curves in response to varying CPAP system requirements in a number of ways, used separately or in conjunction with one another. Generally, such tuning can be achieved by altering the ratio between the maximum gas flow area and the minimum gas flow area and/or altering the resistance of the movable portion 12 to movement as a function of the pressure of the gas. Thus, vent 10 can be tuned by 1) altering the pivot angle of the movable portion 12 with respect to the fixed portion 14 in the relaxed position; 2) altering the ratio of the area of the orifice 20 with respect to the outer periphery 18 of the movable portion 12; 3) altering the shape or size of the orifice 20 and/or outer periphery 18; 4) changing the vent material to provide a different rigidity; 5) altering the thickness of the vent 10 to change rigidity; and/or 6) altering the cross-sectional area and/or configuration of the hinge 16 to alter rigidity. Other methods can also be used to change the tuning of the vent, including, for instance, different heat treatment procedures for vents made of metal, etc.

In addition, one or more apertures of various shapes can be provided on the movable portion 12 to alter the rigidity of the movable portion 12 and/or alter a surface pressure gradient on the movable portion 12 when exposed to the pressurized gas. Of course, if a desired minimum bleed flow is desired that is not provided for by the clearance between the orifice 20 and the outer periphery 18, one or more bleed orifices 24 and/or 26 can be provided in the movable and fixed portions, respectively. Further, it is also contemplated that a multi-stage vent could be provided by utilizing a plurality of movable portions with different operating parameters in conjunction with respective fixed portion orifices or even to provide a second movable portion/orifice combination on the movable portion 12 itself. In any of these alternatives, it may also be desirable to provide positive operating stops on either the fixed or movable portions to positively limit travel of the movable portion in either direction. However, the use of positive stops may be avoided where their addition would increase noise (when the stops engage/disengage) to an extent that would be considered undesirable.

In a preferred embodiment, the vent 10 is constructed from a unitary sheet of material such as stainless steel or other metal or plastic, although other materials exhibiting the desired combination of rigidity, flexibility, springiness and resistance to bending fatigue can also be used. In such an embodiment, the vent can be formed by stamping, laser cutting, water jet cutting, and molding or by other known methods. In one preferred embodiment, the vent is cut from a single sheet of 0.1 mm thick polyester film of the type conventionally used for overhead projector transparencies. Such film can be obtained from the Orbit company in Australia, as well as from other suppliers such as 3M and Xerox. In this embodiment, the movable portion has an outer diameter of 13 mm and the fixed portion has an outer diameter of 20 mm (although this is not critical), with a gap between the movable and fixed portions of 0.2 mm.

The shape of the vent need not be circular but can be any desired shape. The shape can even be asymmetrical so that it can only be positioned in the base portion in the correct orientation, i.e., with the movable portion 12 pivoted toward the mask/gas supply tube in the relaxed position and not toward the atmosphere. Alternatively, a correct orientation of the vent can be assured by providing an outer edge of the fixed portion with asymmetrically positioned notches or tabs to engage similarly positioned tabs/notches provided in the base portion. In an alternative embodiment, the movable portion and fixed portion can be separate components affixed to one another through use of a hinge on either component or even through use of a separate hinge. In addition, the resistance of the movable portion to movement can be increased by utilization of an auxiliary spring member, which, in a simple form, could merely be an additional piece of rigid material overlaying and attached to the hinge 16. By providing a readily removable cover 40 over the vent 10, the flow rate characteristics of the mask can be easily and inexpensively tailored to an individual's clinical need, merely by exchanging the vent 10 with an alternative vent 10 having different operating parameters. In addition interchangeable flaps and covers with orifices to atmosphere may be substituted so as to change operating parameters.

Figure 9:
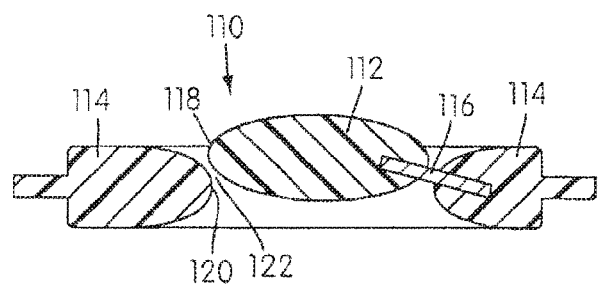
FIG. 9 is a sectional view of an alternative embodiment of the flow regulation vent of the present invention.

The vent also need not be essentially flat, as in the present embodiment, but can have different profiles as appropriate. For instance, the vent can have a convex or concave profile. Furthermore, the thicknesses of the movable portion and/or the fixed portion can be increased and the edges of the orifice and/or movable portion can be rounded to provide a smoother gas flow through the vent, with potential gains in noise reduction. In one such embodiment, as shown in FIG. 9 in the fully pressurized position, the rounded outer periphery 118 of the movable portion 112 of vent 110 can even overlap the rounded inner edge of the orifice 120 in the fixed portion 114, with opposing surfaces of the two portions configured in a complementary manner to smooth airflow through the gap 122 therebetween. In such thicker, rounded embodiments, the movable and fixed portions would preferably be manufactured as separate components and would be pivotally connected together by a separate hinge that can be made of a different material. For instance, the movable and fixed portions 112 and 114 could be made of molded plastic and the hinge 116 made of metal and attached to the other components with adhesive. A small, polymeric bumper can be attached to one of the portions 112, 114 in the gap 122 to reduce noise should the two portions contact one another in the fully pressurized position.

In a preferred embodiment, the base and cover are made from machine grade polycarbonate, preferably clear. Such material can be obtained from the Dotmar company in Sydney. Australia. An alternative material is Bayer Makrolon 2458 clear polycarbonate by Bayer AG. Other materials from other suppliers can also be used.

FIG. 1 shows an exploded perspective view of an alternative embodiment of the flow regulation vent assembly. In this embodiment, a pin 62 that is mounted or molded to the cover 40 contacts an edge of the movable portion 12 to push the movable portion open into the relaxed position. The pin 62 is preferably positioned at an edge of the movable portion 12 approximately 30° around the perimeter of the movable portion 12 from the hinge 16. A tab 64 on the fixed portion 14 engaging a slot 66 on the cover 40 provides the correct rotational orientation of the movable portion 12 with respect to the pin 62. The height of the pin 62 is determined to provide the desired lift to the movable portion. The pin 62 holds the movable portion in the open position until the pressure in the mask starts to rise and the movable portion starts to close. Since the movable portion and hinge are relatively flexible the movable portion will bend and move toward the fully pressurized position. In this embodiment, the pin 62 prevents the movable portion from being completely coplanar with the fixed portion in the fully pressurized position. Nonetheless, the effective flow area through the vent is still reduced sufficiently to reduce the flow rate through the vent as pressure increases (as compared to a conventional fixed area vent). An advantage of this embodiment is that use of the pin 62 provides an exacting positioning of the movable portion in the open, relaxed position, which can be important when making the vent from thin plastic. Thus, the movable portion need not be pre-formed to be in the open state but can be pre-formed to be in a closed state, with the pin moving the movable portion to the open state. Another advantage of this embodiment is that the vent can be symmetrical from side to side so that either side can be placed toward the mask. In an alternative embodiment, the pin 62 can be replaced by a curved or sloped ramp.

Figure 10:
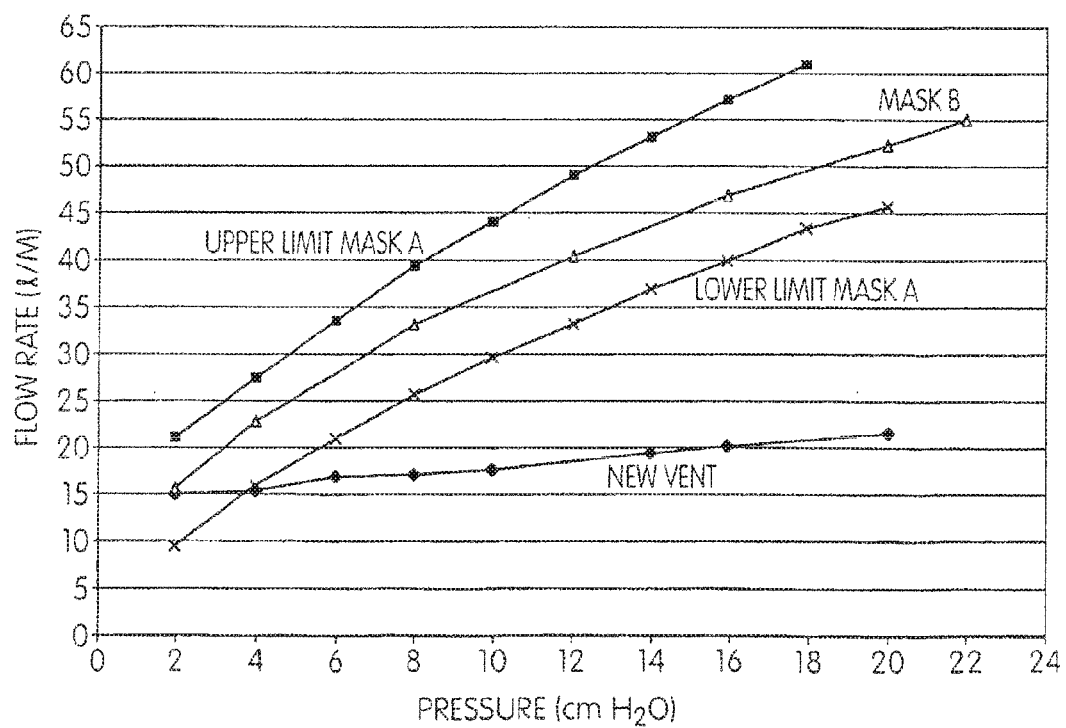
FIG. 10 is a graph of flow rate vs. pressure of a mask utilizing the vent of the present invention in comparison to conventional masks.
Figure 11:
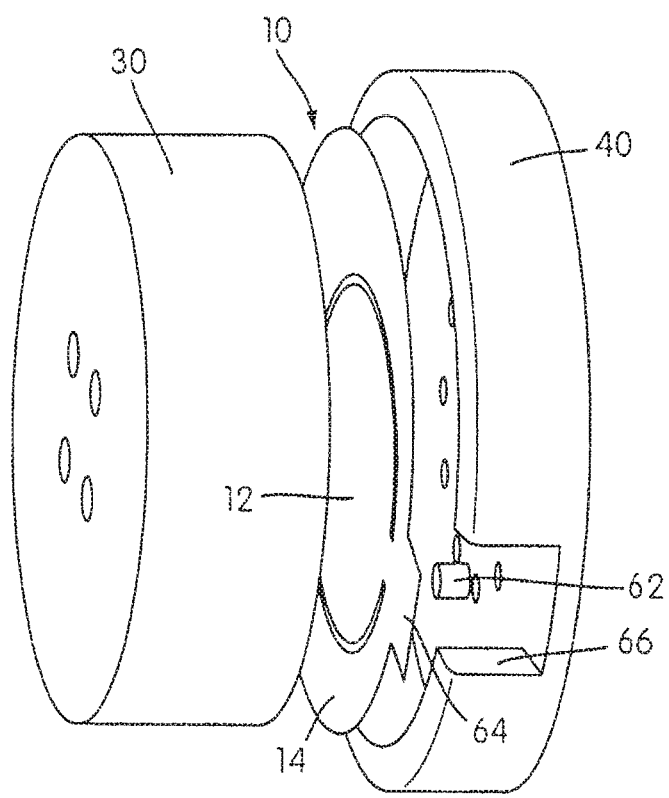
FIG. 11 is a perspective exploded view of an alternative embodiment of the present invention.

Although the preferred embodiments discussed above utilize a movable portion that is positioned in the interior of the fixed portion, it is contemplated that a reverse configuration can be used where the exterior portion of the vent is movable and the interior portion is fixed to the base portion or cover. It is also contemplated that different vent embodiments can be created utilizing different combinations of alternative structures discussed herein. FIG. 10 shows a comparison of the performance of the preferred embodiment vent with conventionally vented CPAP masks "A" and "B". As can be seen, the conventional masks "A" and "B" have sharply increasing flow rate curves while a mask utilizing the vent of the present invention has a less steep flow rate curve. Thus, at 16 cm $H_2O$, the mask utilizing the flow regulation vent of the present invention has a flow rate of approximately half of the lower limit flow rate of conventional mask "A" at 16 cm $H_2O$ and a flow rate of less than half of the average flow rate of conventional mask "B" at 16 cm $H_2O$.

Additional testing has shown that with a bilevel CPAP system such as VPAP II by ResMed Limited, a shortened rise time to the target mask pressure from when the patient begins inspiration is achieved using the present invention vent, as compared to a mask using a conventional fixed area vent. If the rise time in pressure is too long, the patient has the feeling of not getting sufficient air upon inhalation. Thus, a shorter rise time is preferred. In one test, the rise time for the present invention vent was approximately 250 ms, as compared to 300 ms in a conventional mask. Achieving the improved rise time performance by incorporating into a CPAP system the vent of the present invention is a less expensive alternative to achieving the same result by increasing flow generator performance.

Testing has also shown that in a CPAP mode where pressure in the mask is desired to remain relatively constant, the present invention vent is effective in doing so, as are conventional fixed flow area vents. Accordingly a vent of the present invention is compatible with constant pressure CPAP and may be used to ensure that a CPAP system delivers adequate exhaled gas wash out across the pressure range notwithstanding that the pressure remains fixed for a given patient during a period of treatment. Furthermore in a mode where the flow generator is shut off, testing has shown that the present invention vent acts as an effective anti-asphyxiation valve, providing pressure in the mask that is substantially the same as if the mask was opened to the atmosphere by removing the gas supply tube 34 from the mask. This is especially important in case of flow generator malfunction to reduce the risk of asphyxiation, or even the perception thereof, by the patient.

The flow regulation vent of the present invention operates to reduce a flow area of the vent as pressure within the mask increases so as to reduce the flow rate of the vent as compared to a conventional fixed area vent. This is accomplished by progressively moving a movable portion of the vent with respect to increasing pressure to progressively reduce a flow area between the movable portion of the vent and a fixed portion of the vent. The progressive movement of the movable portion can be accomplished by applying a spring force to the movable portion to progressively resist movement of the movable portion accompanying the increasing pressure.

In a modification of the present invention, a strain gauge 60 can be optionally attached by known means between the movable portion 12 and the fixed portion 14 to determine a pivot angle between the movable portion 12 and fixed portion 14. See FIGS. 1-3. If the vent 10 is constructed of plastic, the strain gauge can be embedded in the vent 10. The measurement of the pivot angle, taken in conjunction with the operating parameters of the vent 10 and the pressure of the gas, can then be used to calculate flow though the vent, thus allowing the vent to also function as a flow meter. Signals indicative of the pivot angle can be processed in the vicinity of the vent, say by a processor located on the mask the gas supply conduit or headgear which secures the mask. Alternatively the processor may be located at a distance from the vent, say at the flow generator or in another location. In all instances the transmission of the signals indicative of the pivot angle from the vicinity of the vent to the processor may be achieved by any suitable means such as by conductive wire, optical or wireless transmission.

Figure 12:
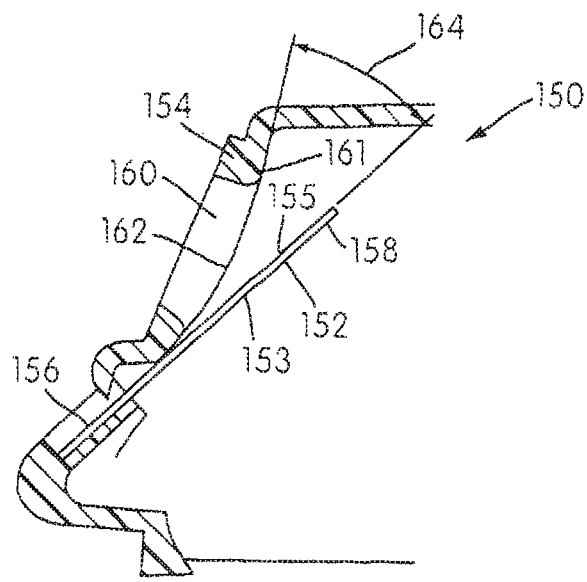
FIG. 12 is a sectional view of an alternative embodiment of a flow regulation vent of the present invention.

An alternative embodiment of the present invention is shown in FIG. 12. In this embodiment, a flow regulation vent 150 includes a flexible flap portion 152 attached at a first end 156 to a fixed housing 154 so that a free end 158 of the flap 152 can move within a given range with respect to the housing 154. Thus, the flap acts as a cantilever arm with the first end 156 fixed and the free end 158 movable. The housing 154 is connected to a mask shell or gas flow conduit. The vent housing 154 can be a separate component attachable to the mask shell or gas flow conduit, or can be integrated with such components. A side 153 of the flap 152 is exposed to an interior chamber of the mask shell or gas flow conduit that is pressurized to a pressure different than the exterior atmospheric pressure when the mask is in use. A side 155 of the flap is positioned toward an atmosphere side of the vent 150. The housing 154 includes a vent orifice 160 positioned beneath the free end 158 of the flap 152. A portion of the housing 154 surrounding the vent orifice 160 is curved to provide a surface 161 having a radius of curvature 162 about a single axis. The flap 152 comes into contact with the housing 154 at the surface 161. As shown in FIG. 12, the flap 152 is in a relaxed state such that the vent orifice 160 is completely uncovered and a gas flow area between the vent orifice 160 and the flap 152 is at a maximum.

While flexible, the flap 152 has a level of natural rigidity that will resist bending of the flap 152 and will provide a spring resistance against bending of the flap. When the mask is in use, a force will act against this spring resistance of the flap 152 and cause the free end 158 of the flap 152 to move toward the vent orifice 160. As the free end 158 of the flap 152 moves closer to the vent orifice 160 with increasing mask pressure, it will follow the radius of curvature 162 of surface 161 of the housing 154, progressively closing the vent orifice 160 and reducing the gas flow area between the vent orifice 160 and the flap 152. The amount the flap 152 can move between the relaxed state and a state where the vent orifice 160 is completely covered is shown as a maximum deflection angle 164, measurable in degrees. As discussed with respect to previous embodiments above, the interaction between the increasing mask pressure and decreasing gas flow area acts to reduce the gas flow rate through the vent 150 as compared to standard fixed flow area vents.

Figure 13:
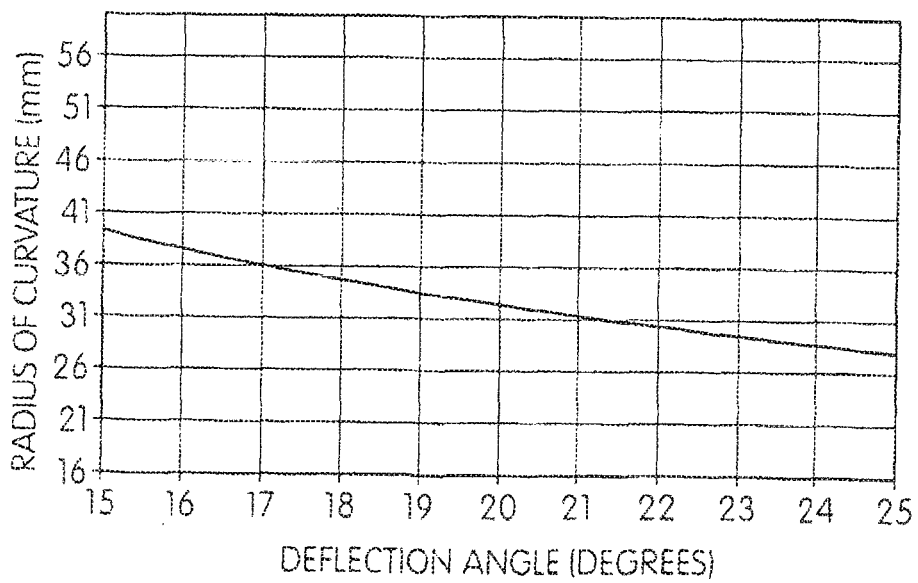
FIG. 13 is a chart showing the relationship between a radius of curvature and a deflection angle for a given pressure at which a flap of the embodiment of FIG. 12 completely closes the vent.

The vent 150 can be tuned to provide different relationships between mask pressure and gas flow area. Such tuning can be accomplished by changing the thickness of the flap 152, the material the flap 152 is made of, or the radius of curvature 162, where a larger radius will allow the flap 152 to progressively close the vent orifice 160 under lower mask pressures as compared to a smaller radius of curvature 162. The curved surface 161 is shown as being convex. However, in alternative embodiments, a concave curved surface can also be used. FIG. 13 shows the relationship between the radius of curvature and the deflection angle for a given pressure at which the flap completely closes the vent. Although other radius of curvature and deflection angles can be used, the chart shows the radius of curvature to be greater than 21 mm and between 26 and 41 mm with the deflection angle between 15 and 25 degrees. The flexing of a flap fixed at one end is governed by the following equation:

$$1/r = L^2 W/(2EI) \tag{Eq. 1}$$

Where:
  r=radius of curvature
  L=length of flap to deflect from an initial position to closing of the vent orifice
  W=uniform load per unit length (air pressure×surface area/length)
    W=Pb where
      P=mask air pressure
      b=flap width
  E=modulus of elasticity of the flap material
  I=section moment of inertia of the flap
    I=bt³/12 where
      t=flap thickness
  L can be expressed in terms of arc radius and angle
    L=ra where
      a=deflection angle in radians By substituting for L in Eq. 1 and solving for angle a, the following equation for the deflection angle of the flap is derived:

$$a = (Et^3/6Pr^3)^{1/2} \tag{Eq. 2}$$

The vent 150 of this embodiment is intended for the use with a mask that requires a higher vent flow rate at low pressure. The vent 150 can be designed to work alone or in combination with a fixed bleed such as a fixed flow area bleed orifice. Where the vent 150 operates alone, it is preferably designed so that the flap 152 does not completely cover the vent orifice 160 and fully close the vent 150 under normal operating conditions.

It is preferable that the flap 152 be constructed of a lightweight material for fast response to pressure changes in the mask. However, the material must have sufficient stiffness to provide a spring bias against pressure changes in the mask yet the working stress of the flap is preferably designed to be below the endurance limit of the material to prevent fatigue failure from the repetitive alternating stress imposed by opening and closing the vent orifice. The strain is preferably designed to be below 1% at maximum deflection to prevent creep failure. The material thickness, material properties and the radius of curvature of the housing mainly control the stress and strain of the flap 152 and one or more of these parameters can be altered to adjust the stress and strain in the flap. The flap material is preferably made of a thin film and of a grade acceptable for medical application. Tolerances in the material thickness are preferably less than 10% to reduce variability in performance.

It is preferred that the curved surface 161 of the housing 154 be of a high finish of 8 micron or better and free of irregularities in order to achieve an airtight seal when the flap 152 is fully closed. The vent orifice 160 can be of any desired shape, including a rectangular window or grouped series of smaller orifices. The use of a symmetrically shaped orifice of constant width and length, such as a rectangle, will make the reduction in cross-sectional area of the vent orifice more uniform as the flap progressively closes the vent orifice. However, the use of an orifice of non-constant width and/or length can be used to specifically tailor the overall flow rate through the vent 150 as mask pressure changes. Fillets of 0.5 mm minimum and draft angles of 3-6 degrees can be used on the vent orifice 160 to reduce air noise.

One specific advantage of this embodiment as compared to known vents is the ability and ease with which the flow characteristics of the vent can be altered at specific pressures within the expected operating pressure range. By altering the characteristics of the housing and flap as discussed above, the flow rate through the vent can be altered depending on the pressure level.

Figure 46:
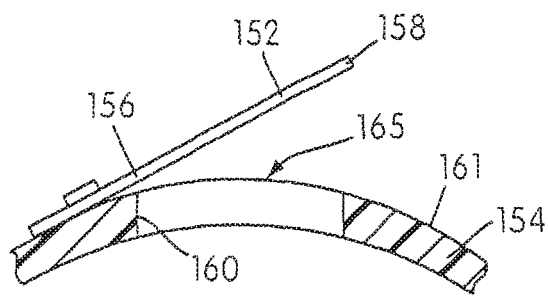
FIG. 46 is a partial sectional view of a modification of the embodiment of FIG. 12.

For instance, in certain situations it may be desirable to quickly reduce flow through the vent as pressure increases above a certain specified pressure level. This can be accomplished by using a housing 154 that has a curved surface 161 with an increasing radius of curvature beyond a point where the flap 152 would be expected to contact the curved surfaced at the specified pressure level. See FIG. 46, where the curved surface 161 of the housing 154 has a first radius of curvature from a fixed end 156 of the flap 152 up to change point 165 and a larger second radius of curvature beyond change point 165. With such embodiments utilizing curved surfaces 161 with an increased radius of curvature beyond a change point, it will take smaller incremental pressure increases above the specified pressure level to bring more of the flap 152 into contact with the curved surface 161 to close more of the orifice 160. Thus, a gas flow area between the flap 152 and the curved surface 161 will decrease at a faster rate above the specified pressure level.

Figure 47:
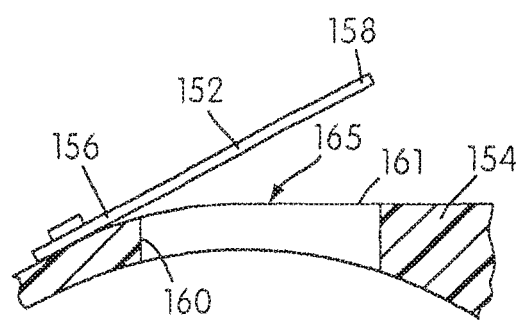
FIG. 47 is a partial sectional view of a modification of the embodiment of FIG. 12.

It is even contemplated that beyond the change point, some embodiments could have flat surfaces 161, i.e., having an infinite radius of curvature. See FIG. 47. In such embodiments, the flap would come into complete contact with the curved surface above the specified pressure level, thereby closing the vent orifice 160 above the specified pressure level. In such an embodiment, venting above the specified pressure level would have to be through a fixed area bleed orifice on the flow regulation vent or mask assembly. It is also contemplated that the radius of curvature of the surface 161 could increase in discrete steps beyond a certain change point 165 or continuously increase beyond a certain change point 165. Under certain circumstances, the radius of curvature can be decreased beyond the change point 165 to provide an opposite effect where the rate of reduction of the gas flow area between the flap 152 and the vent orifice 160 decreases beyond the change point as the pressure increases.

Figure 48:
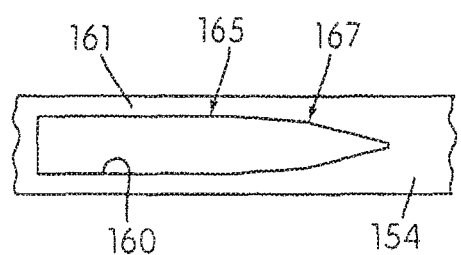
FIG. 48 is a partial top plan view of a modification of the housing of the embodiment of FIG. 12.

A similar result can be achieved by reducing the cross-sectional area of the vent orifice 160 beyond the change point 165. See FIG. 48 where the width of the orifice 160 begins to decrease at change point 165 and decrease further at second change point 167. In this embodiment, the gas flow area between the flap 152 and the vent orifice 160 will decrease at an increasing rate beyond change point 165 (associated with a first specified pressure level) and decrease at an even faster rate beyond second change point 167 (associated with a second specified pressure level). The change in width of the orifice 160 can be at one or more discrete points, can be continuous within specified ranges or can be increasing or decreasing within specified ranges. The change in cross-sectional area of the vent orifice can also be accomplished by positioning an insert of a desired width profile in the vent orifice 160 to effectively alter the width of the vent orifice. As with the example above, the opposite effect can also be accomplished by reducing a width of the vent orifice 160 before the change point 165. Where the vent orifice 160 comprises a plurality of smaller spaced apart orifices, the effect can be achieved by altering the area of one or more of the orifices with respect to the other orifices as they) are positioned further from the fixed end 156 of the flap 152.

Figure 49:
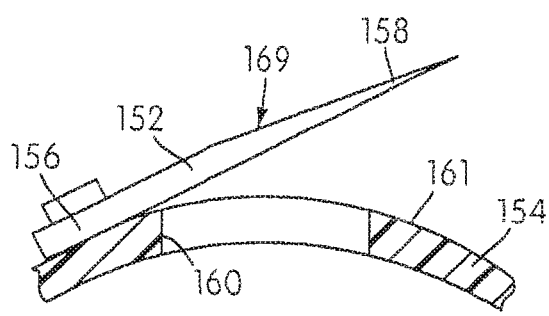
FIG. 49 is a partial sectional view of a modification of the embodiment of FIG. 12.

A similar result can be achieved by reducing the thickness (and thus rigidity) of the flap 152 beyond a change point 169 on the flap 152. See FIG. 49. In this embodiment, the less rigid outer portion of the flap 152 will flex more easily toward the curved surface 161 beyond change point 169 (associated with a specified pressure level) and close the vent orifice 160 at a faster rate. The opposite effect can be achieved by increasing the rigidity of the flap 152 as one or more points outboard of the fixed end 156. The change in thickness can be at one or more discrete points, can be continuous within specified ranges or can be increasing or decreasing within specified ranges. Of course, the rigidity of the flap 152 can be altered along its length in other manners as well, such as by the use of an auxiliary stiffening rib of varying rigidity in conjunction with the flap 152 to achieve the same results.

One or more of these tuning mechanisms can be used in conjunction with each other to readily and effectively provide an unlimited ability to precisely tune the gas flow characteristics of the flow regulation vent 150 at any point within an anticipated operating pressure range.

The flap can be attached to the housing by riveting, screwing, clamping, use of adhesive or other known methods. The flap can also be attached to the housing by being positioned in a slot in the housing, the slot preferably forming a friction fit between the housing and the flap.

In general, the vent of this embodiment will operate under the following conditions. A large deflection angle will cause higher initial airflow through the vent, but will delay closure of the vent. A large radius of curvature will cause the flap to close at lower pressure. A large vent will cause higher initial airflow and the size of the vent orifice is limited by the ability of the flap to seal the vent orifice with no deformation. In masks utilizing a fixed area bleed vent, the end of the flap 152 can extend beyond the end of the vent orifice 160 in order to maintain positive air pressure acting on the flap to keep it closed at high pressure once it is shut. An overlap of 1 mm or greater is considered adequate. A bleed vent can be provided in the flow regulation vent by undercutting a portion of the surface 161 through to the vent orifice 160 such that the undercut potion can still flow gas to the vent orifice 160 even when the flap is in complete contact with the surface 161. A bleed vent can also be provided by placing an orifice in the flap 152 that allows gas to flow though the flap 152 to the orifice 160 even when the flap 152 is in complete contact with the surface 161.

The flap 152 is preferably made of a material such as polyester film. The film can be slit to size, and then cut to length. Holes can be punched in the film for location purposes. The housing is preferably made of a moldable clear material for ease of cleaning and visibility. In a preferred embodiment, the vent 150 is detachable from the mask or gas flow conduit. This facilitates replacement in case of damage, the ability to fine tune vent operation for specific applications and the ability to upgrade with improved designs.

Figure 14:
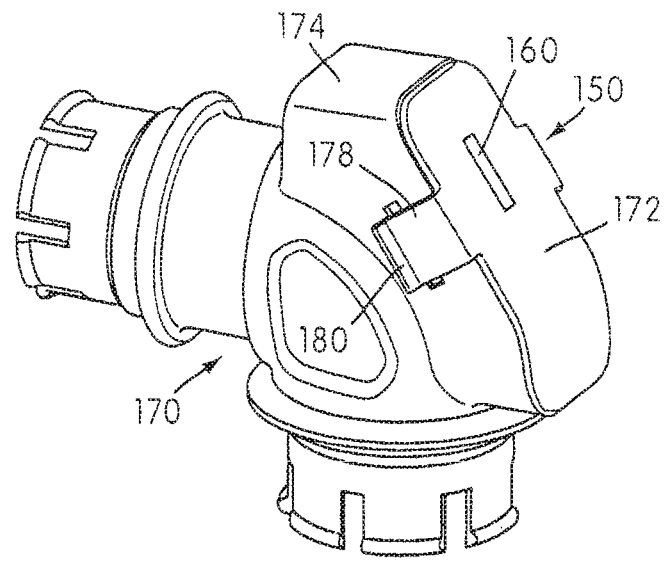
FIGS. 14 and 15 are perspective views of an alternative embodiment of a flow regulation vent of the present invention.
Figure 15:
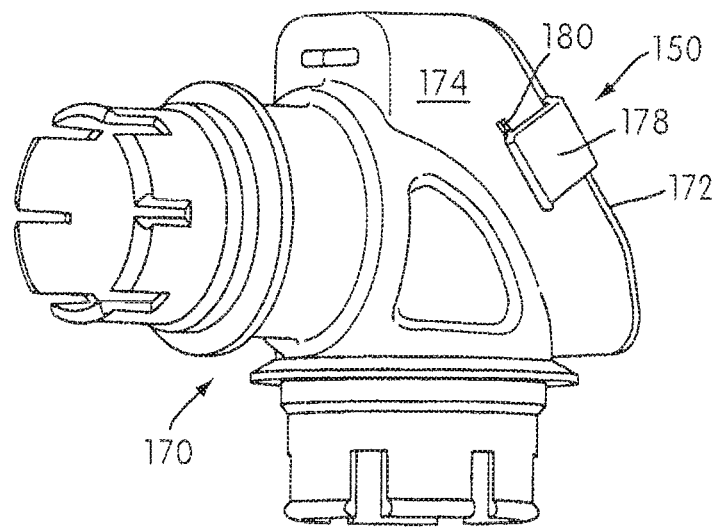
Figure 16:
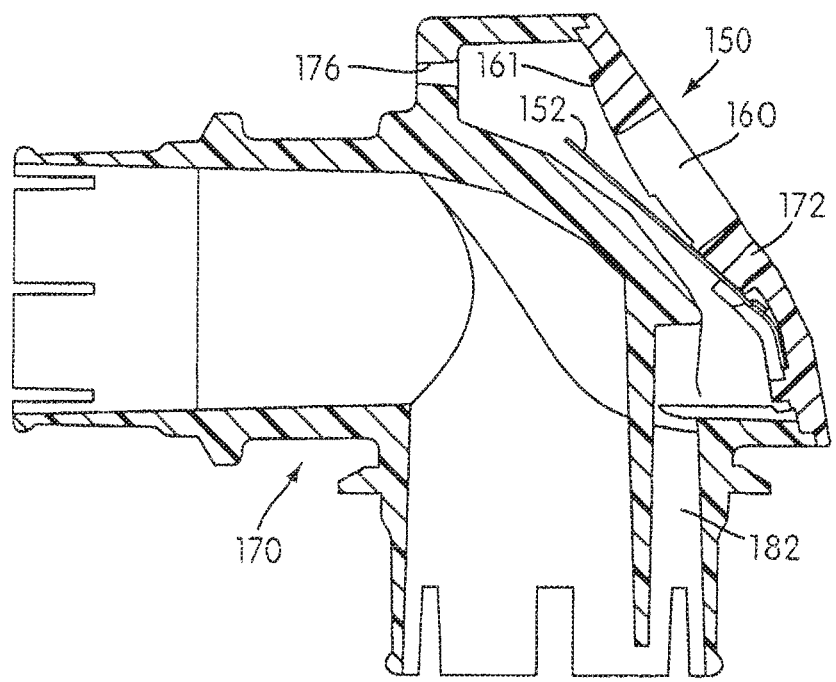
FIG. 16 is a sectional view of the embodiment of FIGS. 14 and 15.
Figure 17:
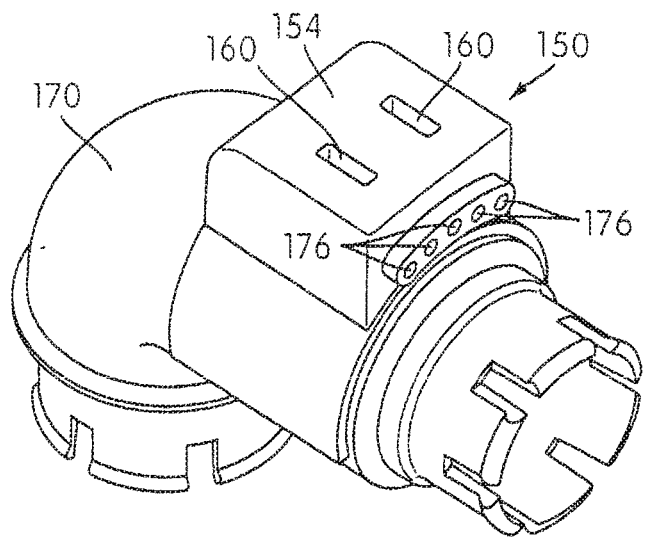
FIG. 17 is a perspective view of an alternative embodiment of a flow regulation vent of the present invention.
Figure 18:
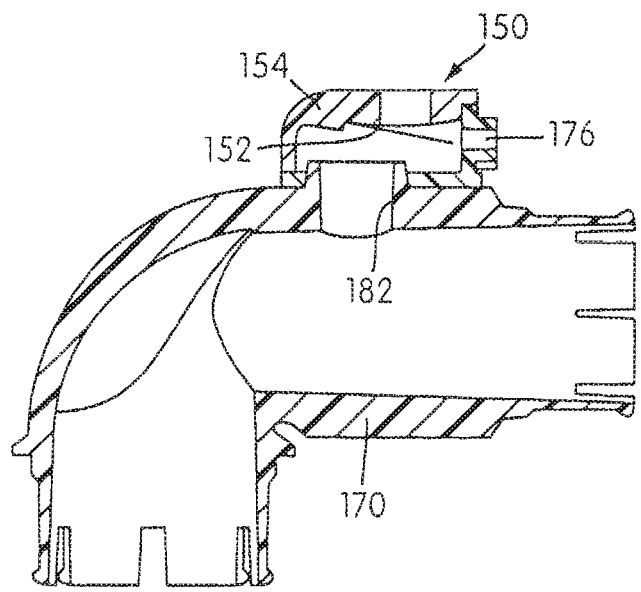
FIG. 18 is a sectional view of the embodiment of FIG. 17.

FIGS. 14-16 disclose an alternative embodiment of the vent 150 mounted to a swivel elbow joint 170 for connecting a gas flow conduit/tube to a mask shell. FIGS. 14 and 15 are perspective views of the vent from different angles and FIG. 16 is a sectional view of the vent 150. In this embodiment, the vent 150 is constructed on a cover 172 used to cover a vent chamber housing 174 mounted on the swivel joint 170. The vent 150 communicates with an interior of the swivel joint 170 and thus, the mask shell, via passage 182. The cover 172 includes snap arms 178 for engaging slots 180 to hold the cover 172 on the housing 174, although other known attachment mechanisms can also be used for this purpose. The vent 150 includes a flap 152, a vent orifice 160 and a curved surface 161 as in the embodiment of FIG. 12 (see FIG. 26). In this embodiment, the vent orifice 160 is rectangular. However, this embodiment also includes a fixed bleed orifice 176 that remains open to provide a minimum vent flow even when the flap 152 completely covers the orifice 160 and the vent 150 is closed. The vent 150 of this embodiment is detachable from the swivel joint 150 for replacement and/or cleaning.

FIGS. 17-26 disclose an alternative embodiment of the vent 150. In this embodiment, the vent housing 154 is formed as a semi-circular clip that can detachably clip onto the swivel elbow joint 170. The vent 150 communicates with an interior of the swivel joint 170 and thus, the mask shell, via passage 182. This embodiment includes two parallel rectangular vent orifices 160 and a plurality of circular fixed bleed orifices 176. Otherwise, the vent 150 of this embodiment operates similarly to the vent 150 of FIGS. 14-16.

Figure 19:
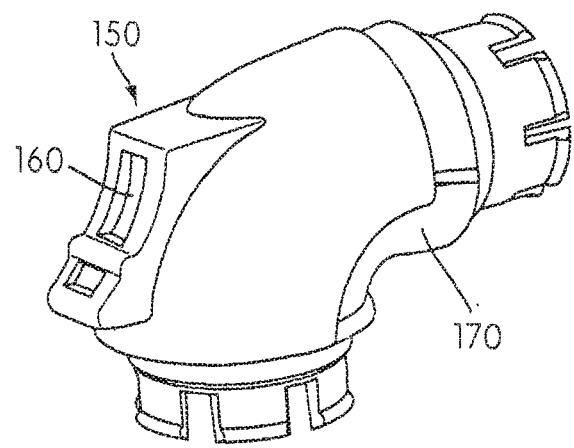
FIG. 19 is a perspective view of an alternative embodiment of a flow regulation vent of the present invention.
Figure 20:
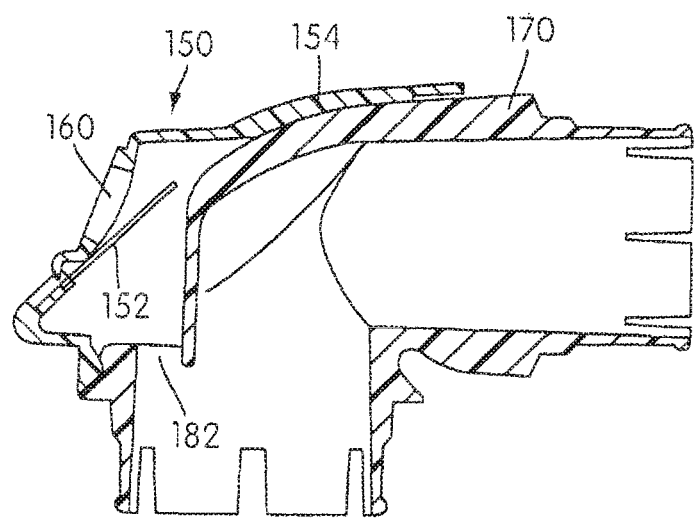
FIG. 20 is a sectional view of the embodiment of FIG. 19.

FIGS. 19-20 disclose an alternative embodiment of the vent 150. In this embodiment, the vent housing 154 is formed as a clip that can detachably clip onto the swivel elbow joint 170. The vent 150 communicates with an interior of the swivel joint 170 and thus, the mask shell, via passage 182. This embodiment includes a single rectangular vent orifice 160 but does not include a fixed bleed orifice. Otherwise, the vent 150 of this embodiment operates similarly to the vent 150 of FIGS. 14-16.

Figure 21:
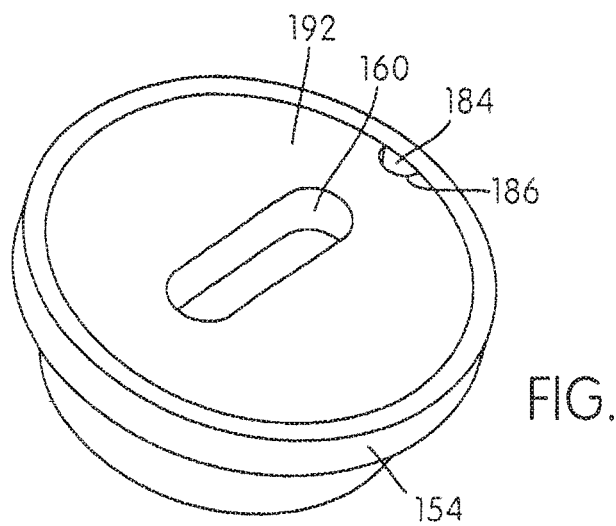
FIGS. 21-23 are perspective views of alternative embodiments of flow regulation vents of the present invention.
Figure 22:
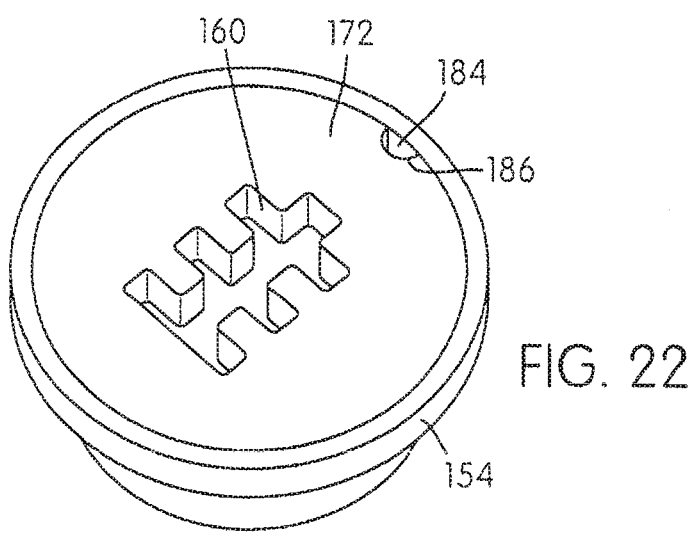
Figure 23:
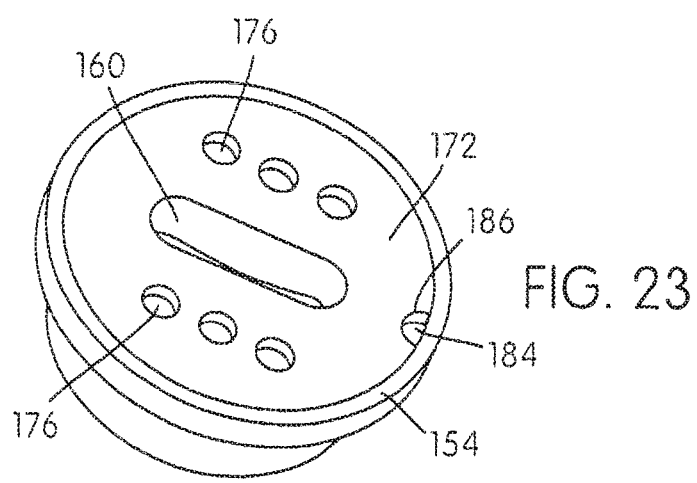

FIGS. 21-23 disclose alternative embodiments of the vent 150. In these embodiments, the vent housing 154 is circular for detachable attachment to a circular mount on a mask shell or gas flow conduit. In the embodiments of FIGS. 21 and 23, the vent orifice 160 is oval shaped. In the embodiment of FIG. 22, the vent orifice 160 is shaped as a series of interconnected channels. The embodiments of FIGS. 21 and 22 do not include fixed bleed orifices while the embodiment of FIG. 23 includes a plurality of fixed bleed orifices 176 that extend in parallel along opposite sides of the orifice 160. In each of these embodiments, the vent orifice is formed on a cover 172 for attachment to the circular housing 154, similarly to the embodiment of FIGS. 14-16. The housing 154 can be provided with an orientation projection 184 for engaging a notch 186 in the cover to rotationally orient the cover 172 with respect to the housing 154. Otherwise, the vent 150 of these embodiments operates similarly to the vent 150 of FIGS. 14-16.

Figure 24:
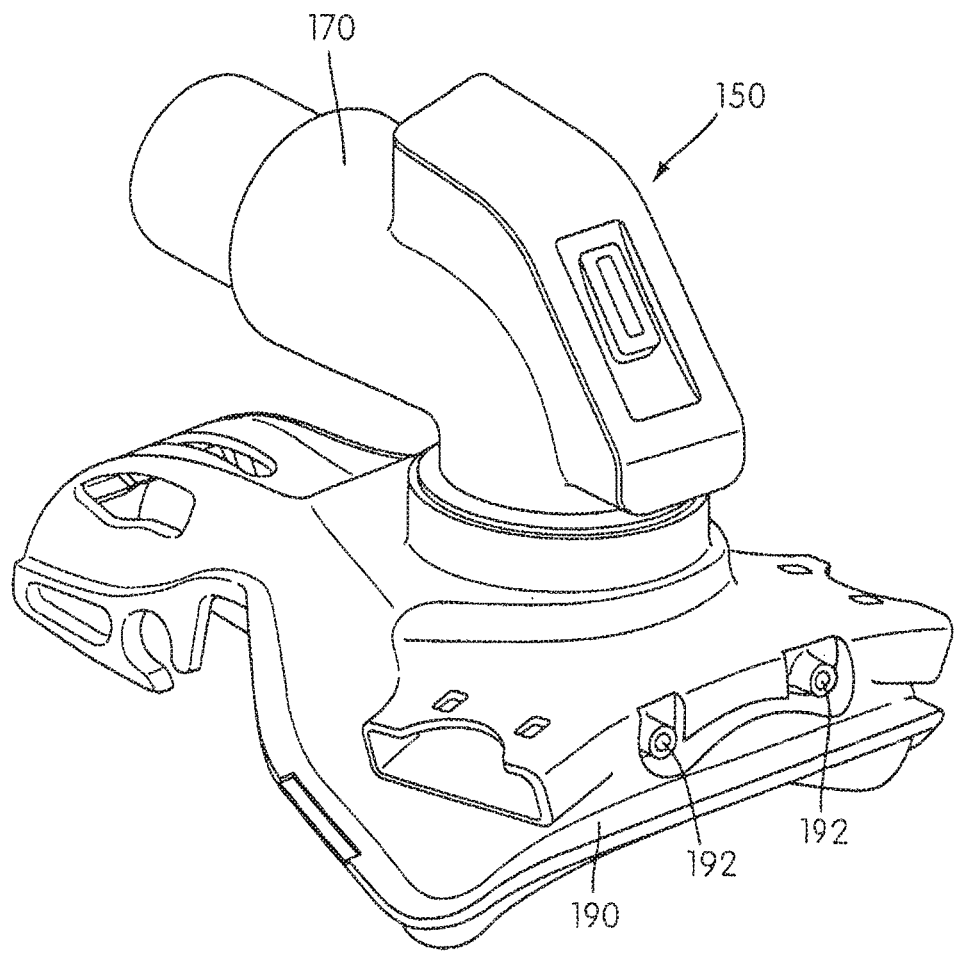
FIG. 24 is a perspective view of an alternative embodiment of a flow regulation vent of the present invention connected to a mask shell.

FIG. 24 discloses an embodiment of a vent 150 similar to the embodiment of FIGS. 14-16, as well as disclosing how the swivel elbow joint 170 is attached to a mask shell 190 of known construction. Mask shell 190 includes a pair of parallel ports 192 that are in fluid communication with the mask interior.

Figure 25:
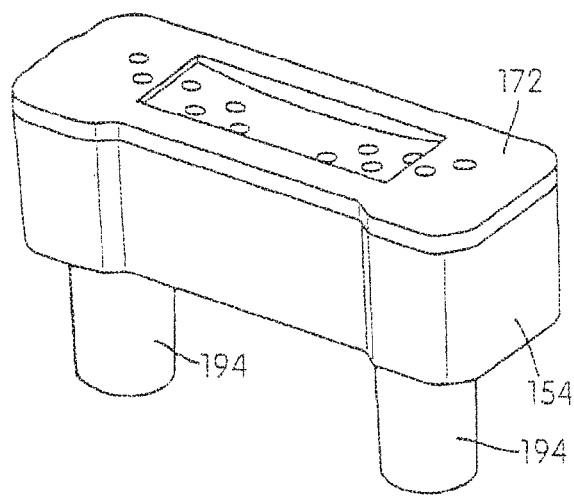
FIGS. 25 and 26 are perspective views of an alternative embodiment of flow regulation vents of the present invention.
Figure 26:
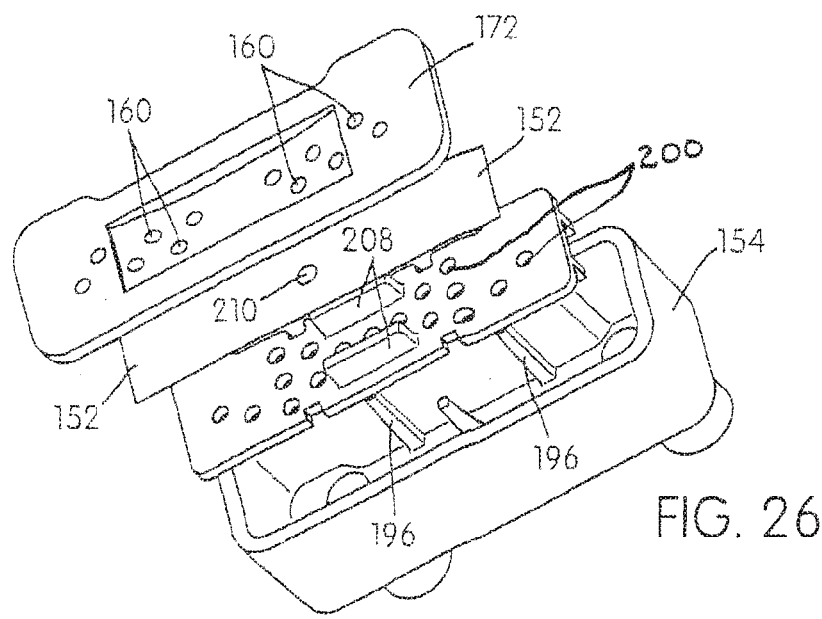
Figure 27:
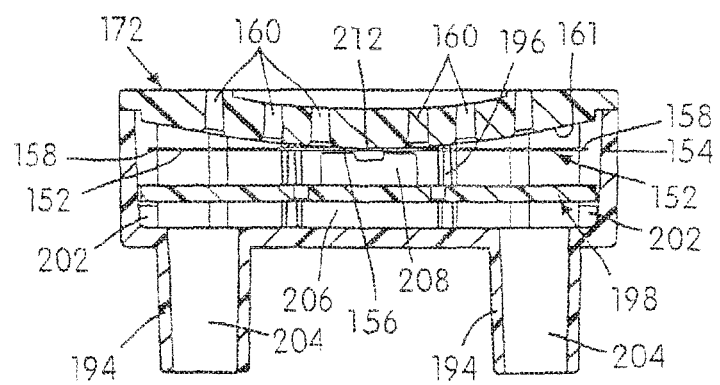
FIG. 27 is a sectional view of the embodiment of FIGS. 25 and 26.

FIGS. 25-27 disclose an alternative embodiment of the vent 150 where the vent housing 154 is generally rectangular in shape and includes a pair of mounting bosses 194 adapted to engage the pair of parallel flow ports 192 (see FIG. 24) to allow flow from an interior of the mask shell 190 to the vent 150. The mounting bosses are sized and configured to be retained on the flow ports 192 by a friction fit, although other known retention mechanisms can also be used. Since the mask shell 190 is of a known design in current production (Ultra MIRAGE® by ResMed Limited), the configuration of this embodiment allows the easy retrofitting of that known mask with the variable vent of the present invention. The housing 154 includes a plurality of internal ribs 196 and seating pads 202 for engaging and positioning a diffuser 198 within the housing 154. As shown in FIG. 27, when the diffuser 198 is properly positioned in the housing 154, a gas chamber 206 is formed that is in communication with passages 204 in bosses 194, which are in turn, in communication with the interior of the mask shell via flow ports 192. The diffuser 198 includes a plurality of orifices 200 through which gas in chamber 206 can pass to flow toward the vent orifice 160. The plurality of spaced-apart orifices 200 acts to diffuse the gas flow from the two passages 204 to more evenly act on the flap 152.

The diffuser 198 also includes a pair of extending retaining walls 208 for engaging a center portion of the flap 152 to position the flap 152 against the convex curved surface 161 of the cover 172. In this embodiment, the flap 152 is not attached to the cover 172 at one of its ends, but rather, flexes from its center to, in effect, create two interconnected flaps 152. The cover 172 includes a centrally located projecting pin 212 to engage a centrally located positioning bore 210 on the flap 152 to position the flap 152 with respect to the cover 172 and prevent lateral movement of the flap 152. The internal ribs 196 of the housing 154 are positioned alongside the flap 152 to prevent the flap 152 from rotating within the housing 154. In an alternative embodiment, the bore 210 and pin 212 can have an asymmetrical configuration to prevent rotation of the flap 152. The flap 152 can also be staked or riveted to the cover 172. The vent cover can be retained to the housing by a snap fit, friction fit, adhesive or other known retention mechanism. The vent cover 172 includes a vent orifice 160 in the form of a plurality of spaced-apart round orifices. This embodiment does not include a fixed bleed orifice but such a fixed bleed orifice can be provided on the vent 150 or elsewhere on the mask shell or gas flow conduit. Otherwise, the vent 150 of this embodiment operates similarly to the vent 150 of FIGS. 14-16, with each outboard side of the flap 152 movable in response to mask pressure to progressively close a respective portion of the vent orifice 160.

Figure 28:
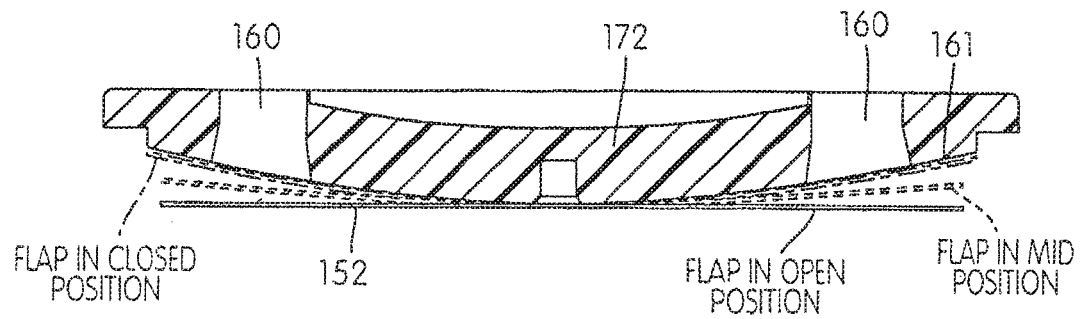
FIG. 28 is a sectional view of a cover and mounted flap of a vent of a configuration similar to the embodiment shown in FIGS. 25-27, with the flap shown in three different positions based on mask pressure exposed to the flap.

FIG. 28 shows a cover 172 and mounted flap 152 of a configuration similar to the configuration shown in FIGS. 25-27, with the flap 152 in three different positions based on mask pressure exposed to the flap 152. In the first position, the flap 152 is entirely open. In the second position, increased mask pressure has moved the outboard ends of the flap 152 toward the convex curved surface 161 of the vent cover 172 to partially obstruct flow through the vent orifices 160. In the third position, mask pressure has increased to the point that the outboard ends of the flap 152 have moved further toward the curved surface 161 to completely close the vent orifices 160. All of the embodiments shown in FIGS. 12-32 operate similarly.

Figure 29:
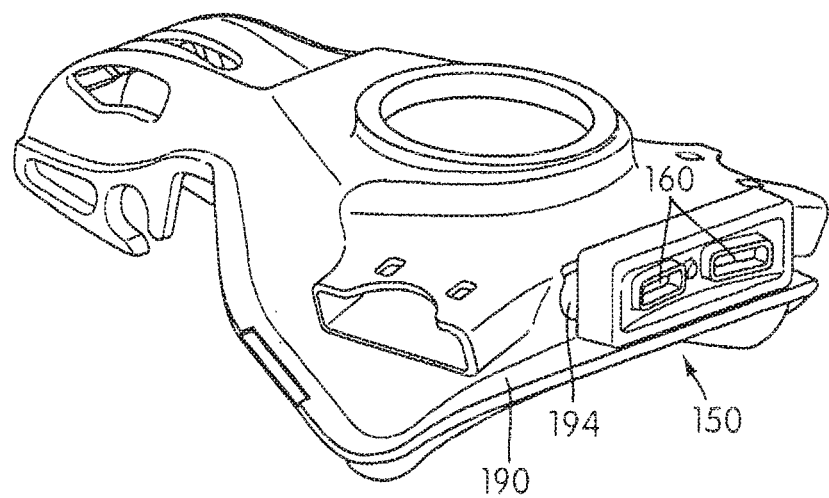
FIG. 29 is a perspective view of a flow regulation vent similar to the embodiment of FIGS. 25-27 connected to a mask shell.

FIG. 29 discloses a mask shell of the type shown in FIG. 24 with a vent 150 similar to the type disclosed in FIGS. 25-28 attached to the flow ports 192. In this embodiment, the vent orifice 160 is configured as two oval orifices.

Figure 30:
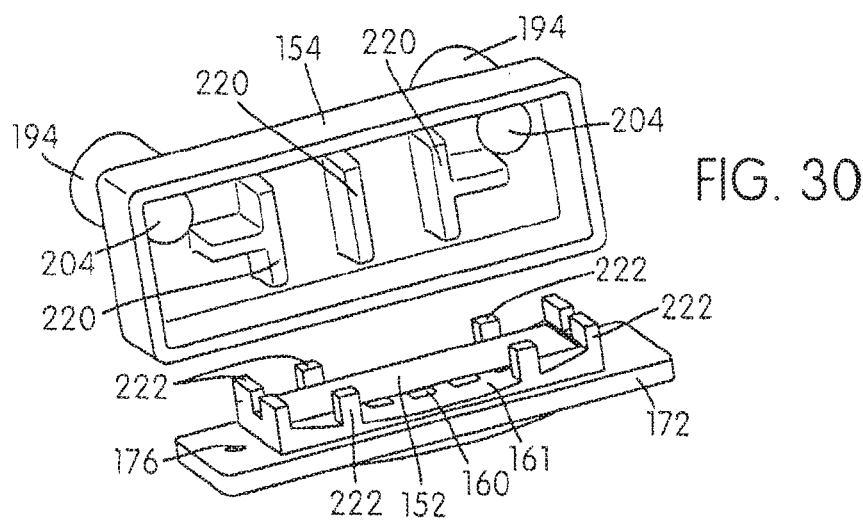
FIG. 30 is an exploded view of an alternative embodiment of a flow regulation vent of the present invention.
Figure 31:
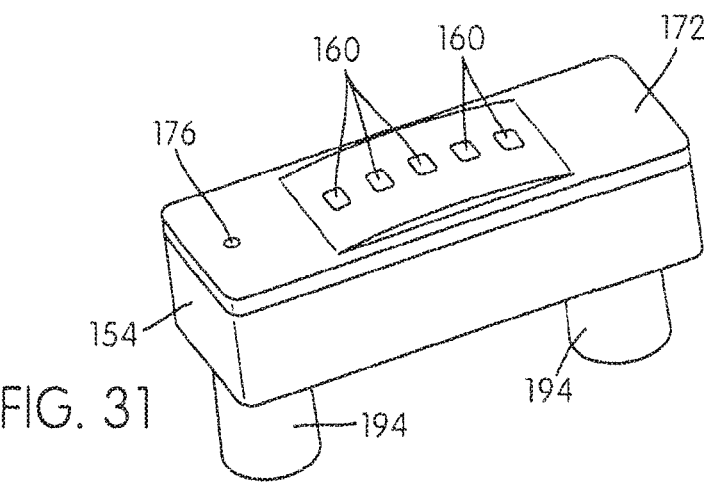
FIG. 31 is a perspective view of the embodiment of FIG. 30.
Figure 32:
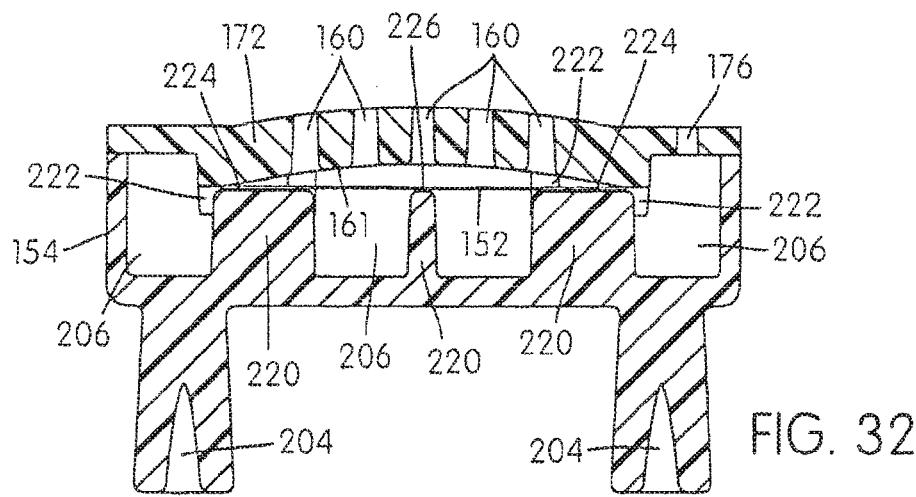
FIG. 32 is a sectional view of the embodiment of FIG. 30.

FIGS. 30-32 disclose an embodiment similar to the embodiment disclosed in FIGS. 25-29 but where the curved surface 161 on cover 172 is concave. In this embodiment, the housing 154 includes a plurality of raised walls 220 connected to an internal floor of the housing 154 to both support the flap 152 and to diffuse air/gas flow from passages 204. The vent cover 172 also includes a plurality of raised posts 222 surrounding the curved surface 161 to position and retain the flap 152 over the curved surface 161. The walls 220 and posts 222 interact to maintain the flap 152 in the desired position over the curved surface 161 when the vent cover 172 is installed on the housing 154, as can be best seen in FIG. 32. In the embodiments shown in FIGS. 12-29, the flap 152 is fixed at its center and the outboard ends of the flap 152 move over the convex curved surface 161 to vary the vent orifice 160. In this embodiment however, the curved surface is 161 is concave and the flap 152 is not fixed to the vent cover 172 at any point. As opposed to the previous embodiments where the flap bends from one fixed end or from the center, in this embodiment, the flap 152 bends from both outboard ends 224 such that the flap center 226 bows toward the concave curved surface 161 under increasing mask pressure to progressively close the vent orifice 160. This embodiment also includes a fixed bleed orifice 176.

Figure 33:
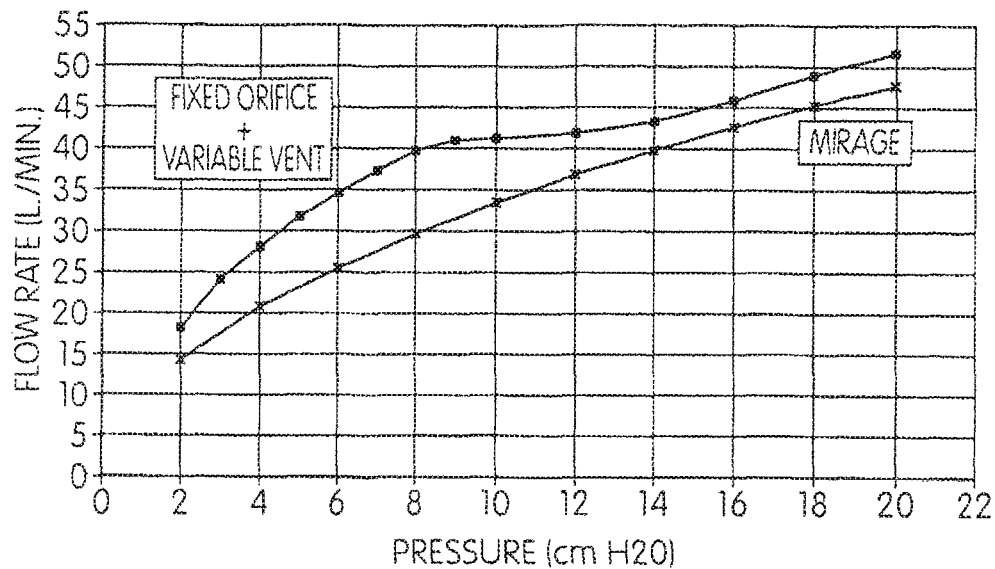
FIGS. 33 and 34 show two charts comparing the flow performance of a standard ResMed™ Mirage® mask with a ResMed™ Mirage® mask utilizing a vent according to one of the embodiments of FIGS. 12-32.
Figure 34:
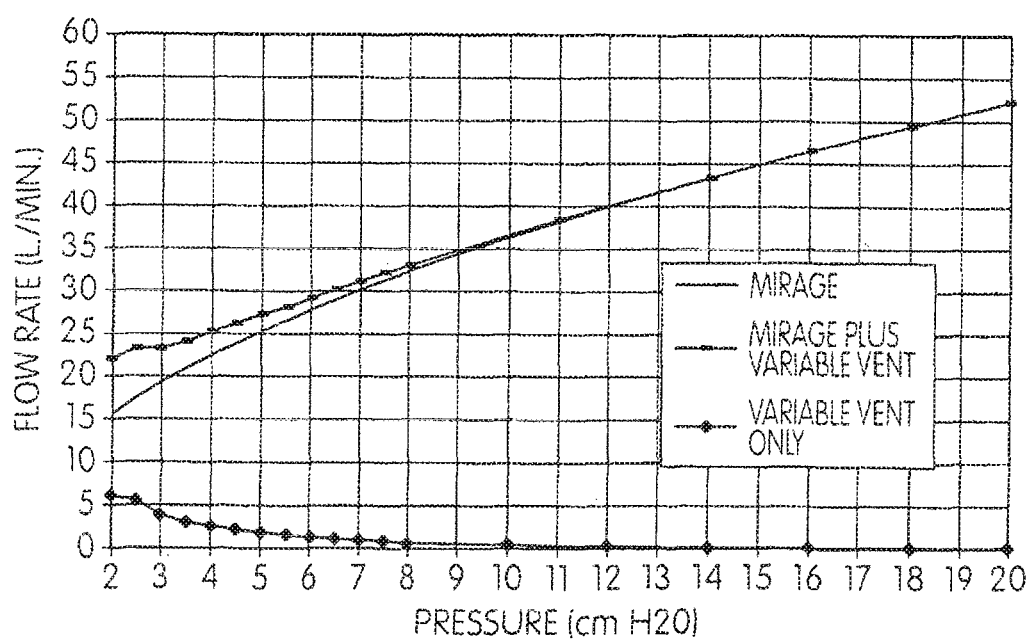
Figure 35:
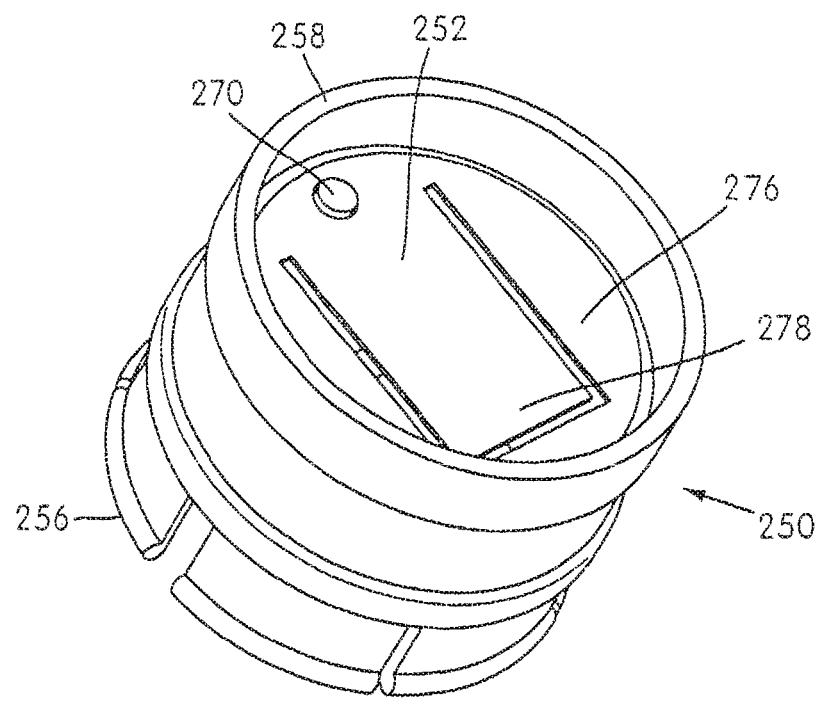
FIG. 35 is a flow generator side perspective view of an alternative embodiment flow regulation vent of the present invention.
Figure 36:
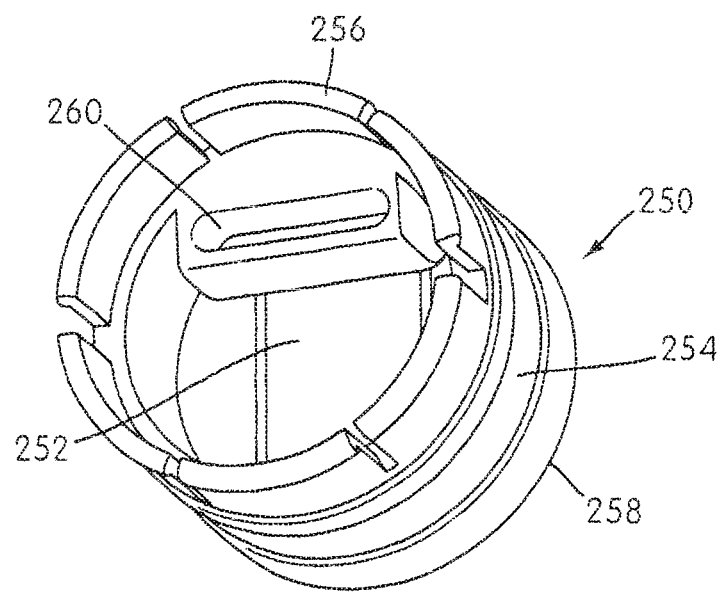
FIG. 36 is a mask side perspective view of the vent of FIG. 35.
Figure 37:
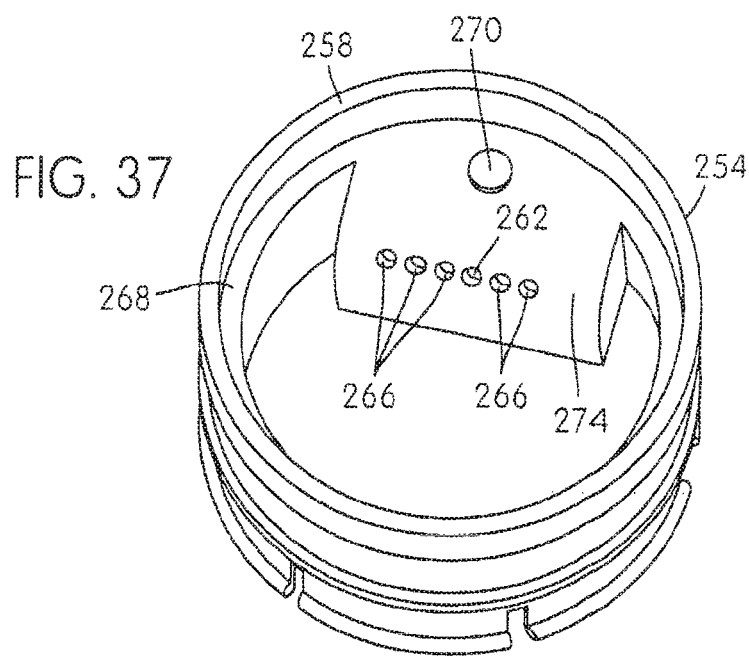
FIG. 37 is a flow generator side perspective view of a housing of the vent of FIG. 35.
Figure 38:
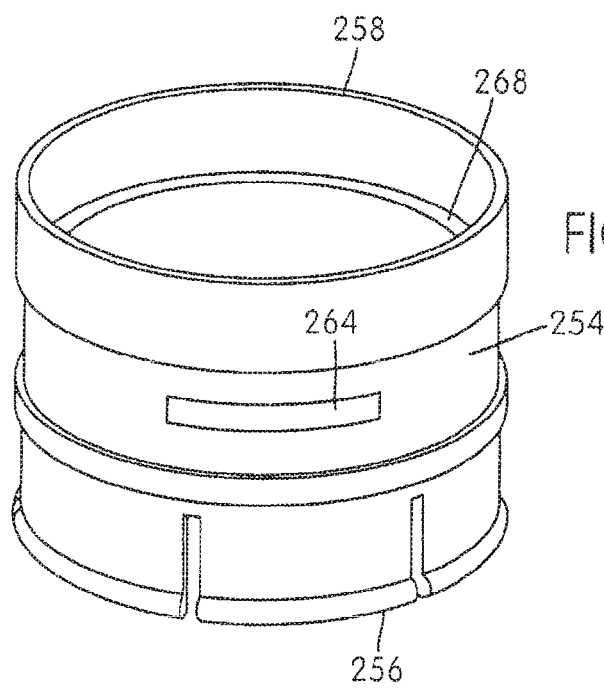
FIG. 38 is a side perspective view of the housing of FIG. 37.
Figure 39:
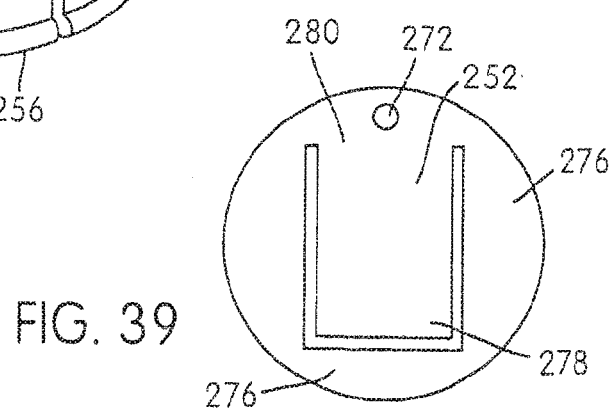
FIG. 39 is a front view of a flap of the vent of FIG. 35.

FIGS. 33 and 34 show two charts comparing the flow performance of a standard ResMed™ Mirage® mask with a ResMed™ Mirage® mask utilizing a vent according to one of the embodiments of FIGS. 12-32. In FIG. 37 the chart shows the flow performance of the mask utilizing a vent 150 (including a fixed bleed orifice 176) as compared to the standard mask. The flow rate for the inventive mask is substantially higher at low mask pressures but tapers off at higher mask pressures to be only slightly higher than the standard mask. In effect, the closing of the variable vent 150 is delayed somewhat as shown by the hump in the curve at lower mask pressures. This delayed closure can be achieved by utilizing a curved surface 161 with a smaller radius of curvature or a thicker, stiffer flap 152.

FIG. 34 shows a comparison between a standard ResMed™ Mirage® mask with a ResMed™ Mirage® mask utilizing a vent according to one of the embodiments of FIGS. 12-32. The solid curve is for the standard mask. The box curve is for a mask continuing to utilize the fixed bleed orifices of the standard mask but also using a variable vent 150 (having no fixed bleed orifice). This curve shows a higher flow rate at lower mask pressures when the variable vent 150 is open but then overlays the standard curve once the variable vent 150 is closed and flow is only through the fixed bleed orifices of the standard mask. The initial hump in the curve was achieved by using a larger flap deflection angle 164 of 22 degrees and a larger radius of curvature 162 of curved surface 161 of 35 mm. The diamond curve is for a mask utilizing only the variable vent 150, with no fixed bleed orifice in the vent 150 or the mask. This curves shows flow at lower mask pressures that decreases as mask pressure rises until the vent 150 completely closes and there is no flow at all.

The flow regulation vent of the present invention is simple and inexpensive to manufacture, especially when cut made from a flat, unitary disk as described above, but provides effective, easily tailored flow regulation. With such an effective flow regulation vent, the flow generator is delivering higher pressure and need not be sized to have the additional capacity to handle increased flow rates at higher pressures, as with conventional CPAP systems. Noise from the flow generator motor can also be reduced since the motor can operate at lower RPM to deliver the reduced volume of high pressure airflow. The vent also acts as a sound barrier, reducing the level of noise from the interior of the mask, including noise created by the flow generator that escapes to the atmosphere. Further, the reduced flow rate at high pressure results in less noise generation from the airflow itself. The vent also reduces rebreathing of $CO_2$ and provides for faster air pressure rise time, increasing the effectiveness of the CPAP treatment. Each of these benefits promotes patient compliance with CPAP treatment.

FIGS. 35-42 show an alternative embodiment of the present invention. A flow regulation vent 250 includes a generally round flap portion 252 and a generally tubular fixed housing portion 254. The fixed housing portion 254 includes a user side 256 adapted to be connected to a mask and a flow generator side 258 adapted to be connected to a pressurized supply of gas from a flow generator to position the flow regulation vent 250 between the mask and the flow generator. The fixed housing portion 254 further includes a primary vent orifice 260 positioned near the user side of the housing and a secondary vent orifice 262 positioned near the flow generator side of the housing 254, each flowingly connected to an exhaust orifice 264 (see FIG. 38) exposed to the atmosphere to allow gas flow between each of the primary vent orifice 260 and secondary vent orifice 262 and the exhaust orifice 264. In the embodiment shown, the secondary vent orifice 262 is in the form of a plurality of smaller orifices 266 but can also have other configurations, as discussed above. See FIG. 37. The secondary vent orifice 262 is positioned on a curved surface 274 of the fixed housing portion 254 and is adapted to engage a movable portion 278 of the flap portion 252.

The fixed housing portion 254 also includes a flap seating flange 268, against which a fixed portion 276 of the flap portion 252 seats and a projecting orientation pin 270 for engaging an orientation orifice 272 in the flap portion 252 for properly orienting the flap portion 252 with respect to the fixed housing portion 254 when the flow regulation vent 250 is assembled. A hinge portion 280 connects the movable portion 278 of the flap portion 252 to the fixed portion 276. In the preferred embodiment, a radially outer portion of the curved surface 274 generally smoothly transitions to the flap seating flange 268 to provide a continuous surface against which the movable flap portion 278 can engage as it moves from a relaxed position to a flexed position.

Figure 40:
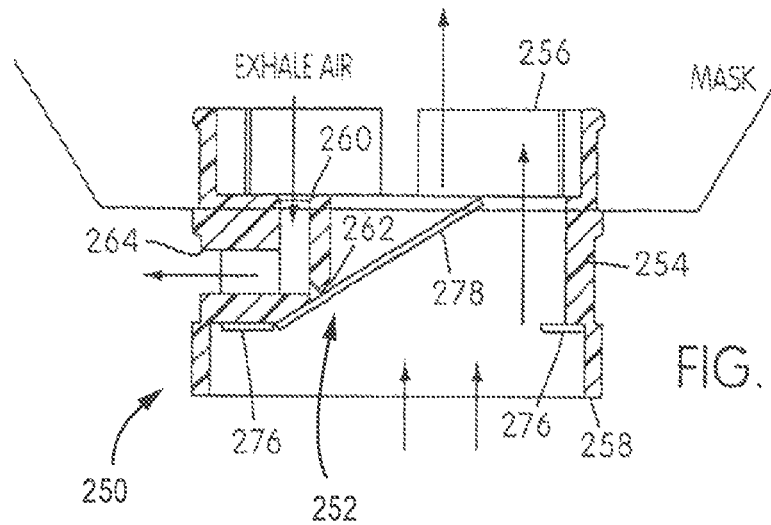
FIGS. 40-42 are partial sectional views of the vent of FIG. 35 showing gas flow through the vent during different stages of operation.

The vent 250 of this embodiment operates as follows, with special reference being made to FIGS. 40-42. FIG. 40 shows the vent 250 during inhalation by the user. The air flow from the flow generator (shown as upward pointing arrows in the Figure) has overcome a natural spring force of the flap 252 to move the movable portion 278 of the flap 252 toward the user, increasing a flow area between the movable portion 278 and the fixed portion 276 of the flap 252. This allows ample air flow to the user during inhalation and prevents any feeling of asphyxiation. The movement of the movable portion 278 has also brought more of the movable portion 278 into contact with more of the curved surface 274 and progressively reduced a flow area between movable portion 278 and the curved surface 274 to reduce flow through the secondary vent orifice 262. This reduces a total flow area through vent orifices 262 and 260 to reduce flow through the exhaust orifice 264 from air flow from the flow generator or from exhalation.

Figure 41:
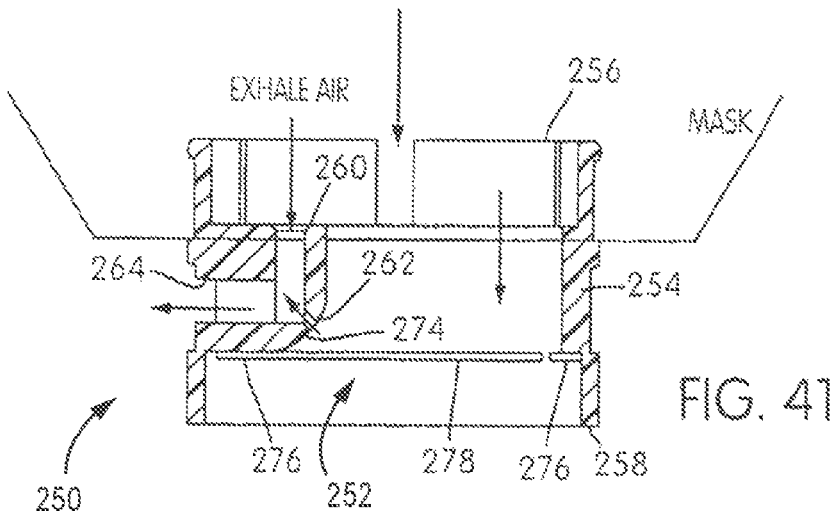

During exhalation, as shown in FIG. 41, the spring force of the flap 252 has returned the movable portion 278 of the flap 252 to a relaxed position, minimizing the flow area through the flap 252. This acts as a non-rebreathing mechanism, minimizing any exhalation into the flow generator conduit and creating $CO_2$ buildup there that will be rebreathed by the user and similarly acts as a one-way valve to prevent oxygen from going back into the flow generator conduit should the flow generator stop working due to malfunction. This also minimizes any incoming gas flow from the flow generator during exhalation. The movement of the movable portion 278 has also uncovered the secondary vent orifice 262 flow area to add that area to that of the flow area of primary vent orifice 260 and increase a total outflow area of the vent 250 for the exhalation gases. With the increased total outflow area, as well as less flow through the total outflow area due to inflow from the flow generator, the exhalation gases can exit the mask at a greater flow rate. This increases $CO_2$ outflow from the mask and decreases undesirable $CO_2$ buildup in the mask. The vent 250 also results in lower mask pressure during exhalation as a result of the increased total outflow area and decreases the pressure rise time in the mask, as compared to conventional masks.

Figure 42:
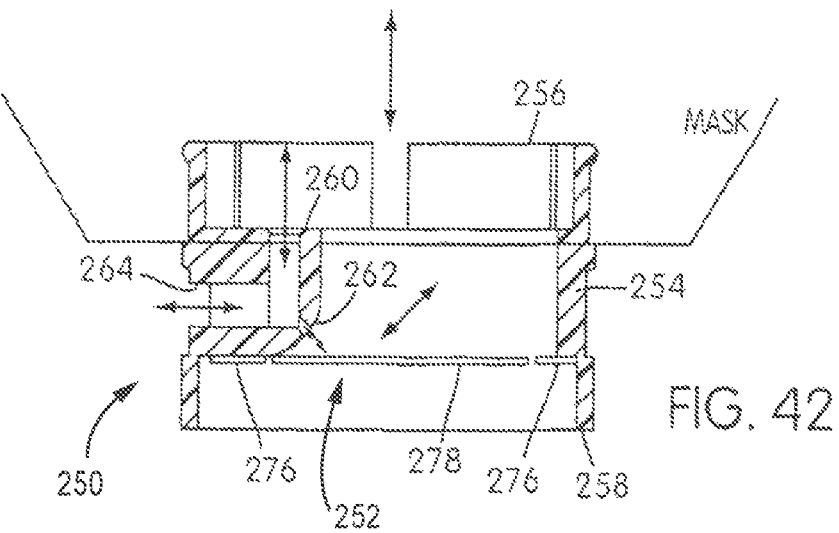

As shown in FIG. 42, the vent 250 also acts effectively as an anti-asphyxia valve in the event that the flow generator ceases operation. In such a situation, the movable portion 278 of the flap 252 remains in the relaxed, closed position, keeping the secondary vent orifice 262 open and increasing the total flow area (in combination with primary vent orifice 260) for allowing outside air into the mask during inhalation by the user. The vent 250 eliminates the need for providing other vents on the mask itself.

Figure 43:
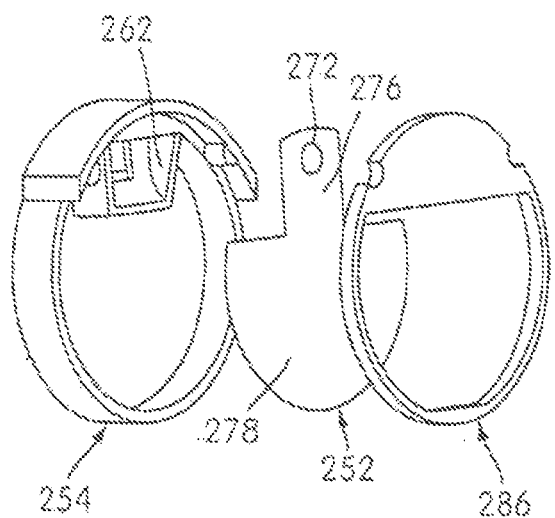
FIG. 43 is an exploded perspective view of an alternative configuration of the vent of FIG. 35.
Figure 44:
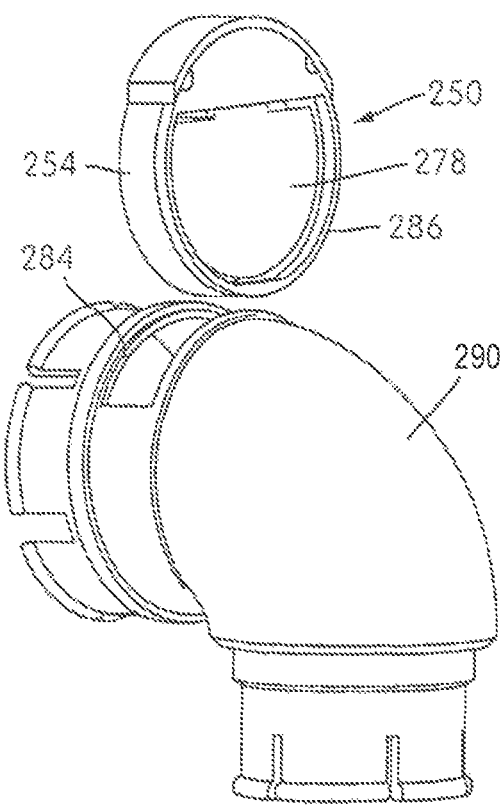
FIG. 44 is an exploded perspective view of the vent of FIG. 43 in combination with a mask elbow joint.
Figure 45:
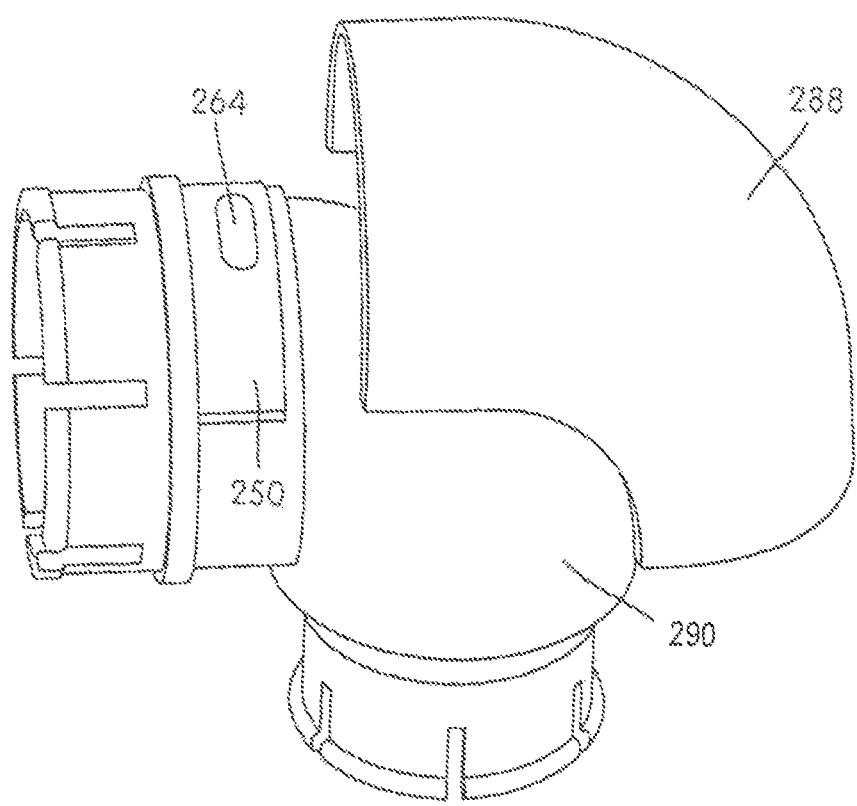
FIG. 45 is a perspective view of the vent of FIG. 43 positioned in a mask elbow joint.

An alternative configuration of the flow regulation vent 250 is shown in FIGS. 43-45. In this configuration, the housing 254 is relatively narrow so that it can be inserted into a slot 284 in a swivel elbow joint 270. The flap 252 is somewhat T-shaped with the movable portion 278 of the flap 252 being a relatively large proportion of the flap 252 and the fixed portion 276 of the flap 252 being a relatively small proportion of the flap 252. In this configuration, the flap 252 is held in place with respect to the housing 254 by a flap cover plate 286 that attaches to the housing 254 and sandwiches the fixed portion 276 therebetween. The cover plate can also be configured to contact a flow generator side of the movable portion 278 when in the relaxed position to prevent reverse flow from exhalation into the flow generator conduit. In this embodiment, the secondary vent orifice 262 is generally rectangular and is not positioned on a curved surface of the housing 254. This is not as important with the flow regulation vent 250 as it is in previous embodiments, since it is not as important to have a progressively increasing or decreasing flow area through the vent orifice 262. Rather, it is more important that the flow area through the vent orifice 262 be small during inhalation and large during exhalation. This embodiment otherwise operates as does the embodiment of FIGS. 35-42. An exhalation flow deflector 288 can be attached to the elbow joint 270 to direct the flow of exhalation gas outside the mask. See FIG. 45. The flap cover plate can be attached to the housing 254 by welding, adhesive, snap fit or other known attachment methods.

In the preferred embodiment, the flap 252 is constructed from thin polyester sheet with a flap diameter of 21.5 mm (positioned in a housing inside diameter of 23 mm), a flap thickness of 0.004 inch and a flap hinge width of 7 mm. The flow characteristics through the vent 250 can be tailored as desired by altering the flap characteristics, including thickness, movable portion area, material and hinge width. A fixed area orifice can also be provided through the vent 250 between the flow generator and the mask to provide flow from the flow generator should the movable portion 278 of the flap become stuck closed. As with embodiments discussed above, the vent 250 can operate as a flow meter by measuring a pressure drop across the vent 250 or by measuring an electrical signal from a strain gauge attached to the flap 252. The orifice 260 can also be configured to provide a high resistance to inflow and a low resistance to outflow.

It is intended that various aspects of the embodiments discussed above can be used in different combinations to create new embodiments of the present invention.

It will be apparent to those skilled in the art that various modifications and variations may be made without departing from the scope of the present invention. Thus, it is intended that the present invention covers the modifications and variations of the invention.

The invention claimed is:

1. A flow regulation vent for use in controlling a vent flow of washout gas to atmosphere in a system for supplying breathable gas pressurized to within a therapeutic pressure range above atmospheric pressure to a patient in the treatment of a sleep disordered breathing condition, the flow regulation vent comprising:
   a housing having at least one vent orifice and at least one fixed bleed orifice; and
   a flap configured to regulate the vent flow of washout gas to atmosphere through the at least one vent orifice,
   wherein the at least one fixed bleed orifice is not covered by the flap in any position and the flow regulation vent provides a minimum vent flow to atmosphere independent of the position of the flap, and
   wherein the at least one vent orifice and the at least one fixed bleed orifice are structured such that the vent flow through the at least one vent orifice and the at least one fixed bleed orifice has a substantially constant flow rate when the breathable gas is pressurized to any pressure within the therapeutic pressure range.

2. The flow regulation vent of claim 1, wherein the flap is configured such that increasing the pressure of the breathable gas within the therapeutic pressure range causes the flap to move and reduce a cross-sectional area of the at least one vent orifice to reduce the vent flow through the at least one vent orifice.

3. The flow regulation vent of claim 2, wherein the at least one vent orifice and the at least one fixed bleed orifice are structured such that the vent flow through the at least one fixed bleed orifice increases in response to a reduction of the vent flow through the at least one vent orifice.

4. The flow regulation vent of claim 1, wherein the therapeutic pressure range is 4 cmH$_2$O to 30 cmH$_2$O.

5. The flow regulation vent of claim 1, wherein the housing further comprises positive operating stops to limit travel of the flap.

6. The flow regulation vent of claim 1, wherein the at least one vent orifice is positioned downstream of the flap relative to the vent flow.

7. The flow regulation vent of claim 1, wherein the flap extends from the housing such that the flap is cantilevered over the at least one vent orifice.

8. The flow regulation vent of claim 1, further comprising a diffuser to diffuse the vent flow.

9. The flow regulation vent of claim 1, wherein the flap has an outer diameter that is greater than a thickness of the flap.

10. The flow regulation vent of claim 1, wherein the at least one vent orifice comprises a plurality of vent orifices, and the at least one fixed bleed orifice comprises a plurality of fixed bleed orifices.

11. The flow regulation vent of claim 1, wherein the flap comprises an elastically deformable material.

12. The flow regulation vent of claim 11, wherein when the flap is not elastically deformed, the flap is configured to not restrict the vent flow through the at least one vent orifice.

13. The flow regulation vent of claim 12, wherein when the breathable gas is pressurized to a pressure within the therapeutic pressure range above atmospheric pressure, the flap is configured to be elastically deformed by the pressure of the breathable gas.

14. The flow regulation vent of claim 13, wherein the flap is configured to elastically deform due to an increase in the pressure of the breathable gas to reduce a cross-sectional area through the at least one vent orifice.

15. A respiratory therapy system for supplying breathable gas pressurized to within the therapeutic pressure range above atmospheric pressure to a patient in the treatment of a sleep disordered breathing condition, the respiratory therapy system comprising:
   a mask configured to provide the breathable gas to the patient's airways;
   a flow generator configured to pressurize the breathable gas;
   a conduit configured to provide the breathable gas from the flow generator to the mask; and
   the flow regulation vent of claim 1.

16. The respiratory therapy system of claim 15, wherein the flow regulation vent is positioned integrally along the conduit.

17. The respiratory therapy system of claim 16, wherein the conduit comprises a circular mount and the housing is circular for attachment to the circular mount.

18. The respiratory therapy system of claim 15, wherein the flow regulation vent is not positioned on the mask.

19. A mask configured to provide breathable gas pressurized to within the therapeutic pressure range above atmospheric pressure to the patient's airways in the treatment of a sleep disordered breathing condition, the mask comprising:
   a shell configured to cover the mouth and/or the nostrils of the patient;
   an elbow joint having a first end configured to be removably and rotatably connected to the shell and a second end configured to be removably connected to a conduit to receive the breathable gas from a flow generator; and
   the flow regulation vent of claim 1,
   wherein the flow regulation vent is integrated with the elbow joint such that the elbow joint and the flow regulation vent are removable from the shell together.

20. A flow regulation vent for use in controlling a vent flow of washout gas to atmosphere in a system for supplying breathable gas pressurized to within a therapeutic pressure range above atmospheric pressure to a patient in the treatment of a sleep disordered breathing condition, the flow regulation vent comprising:
   a fixed portion having at least one vent orifice and at least one fixed bleed orifice; and
   a movable portion positioned adjacent to the fixed portion and configured to be moved by pressure of the breathable gas to regulate the vent flow of washout gas through the at least one vent orifice such that in any position the movable portion does not cover the at least one fixed bleed orifice to provide a minimum vent flow to atmosphere independent of the position of the movable portion, and
   wherein the at least one vent orifice and the at least one fixed bleed orifice are structured such that the vent flow through the at least one vent orifice and the at least one fixed bleed orifice has a substantially constant flow rate when the breathable gas is pressurized to any pressure within the therapeutic pressure range.

21. The flow regulation vent of claim 20, wherein the movable portion comprises an elastically deformable material.

22. The flow regulation vent of claim 21, wherein when the movable portion is not elastically deformed, the movable portion is configured to not restrict the vent flow through the at least one vent orifice.

23. The flow regulation vent of claim 22, wherein when the breathable gas is pressurized to a pressure within the therapeutic pressure range above atmospheric pressure, the movable portion is configured to be elastically deformed by the pressure of the breathable gas.

24. The flow regulation vent of claim 23, wherein the movable portion is configured to elastically deform due to an increase in the pressure of the breathable gas to reduce a cross-sectional area through the at least one vent orifice.

25. The flow regulation vent of claim 20, wherein the therapeutic pressure range is 4 cmH$_2$O to 30 cmH$_2$O.

26. The flow regulation vent of claim 20, wherein the fixed portion further comprises positive operating stops to limit travel of the movable portion.

27. A respiratory therapy system for supplying breathable gas pressurized to within the therapeutic pressure range above atmospheric pressure to a patient in the treatment of a sleep disordered breathing condition, the respiratory therapy system comprising:
- a mask configured to provide the breathable gas to the patient's airways;
- a flow generator configured to pressurize the breathable gas;
- a conduit configured to provide the breathable gas from the flow generator to the mask; and
- the flow regulation vent of claim 20.

28. The respiratory therapy system of claim 27, wherein the flow regulation vent is positioned integrally along the conduit.

29. The respiratory therapy system of claim 28, wherein the conduit comprises a circular mount and the fixed portion is circular for attachment to the circular mount.

30. A mask configured to provide breathable gas pressurized to within the therapeutic pressure range above atmospheric pressure to the patient's airways in the treatment of a sleep disordered breathing condition, the mask comprising:
- a shell configured to cover the mouth and/or the nostrils of the patient;
- an elbow joint having a first end configured to be removably and rotatably connected to the shell and a second end configured to be removably connected to a conduit to receive the breathable gas from a flow generator; and
- the flow regulation vent of claim 20,
- wherein the flow regulation vent is integrated with the elbow joint such that the elbow joint and the flow regulation vent are removable from the shell together.

* * * * *